(12) United States Patent
South et al.

(10) Patent No.: US 10,176,300 B1
(45) Date of Patent: Jan. 8, 2019

(54) FACILITATING PATIENT MONITORING

(71) Applicant: ALLSCRIPTS SOFTWARE, LLC, Chicago, IL (US)

(72) Inventors: Kimberly South, Springfield, IL (US); Jim Hewitt, Springfield, IL (US); John Pacione, Springfield, IL (US); Skyler Wason, Raleigh, NC (US); Jason Petit, Springfield, IL (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 367 days.

(21) Appl. No.: 14/320,267

(22) Filed: Jun. 30, 2014

Related U.S. Application Data

(60) Provisional application No. 61/943,375, filed on Feb. 22, 2014, provisional application No. 61/943,397, filed on Feb. 23, 2014.

(51) Int. Cl.
*G06F 19/00* (2018.01)
*G16H 10/60* (2018.01)

(52) U.S. Cl.
CPC ......... *G06F 19/3418* (2013.01); *G16H 10/60* (2018.01)

(58) Field of Classification Search
CPC .............. G06F 3/04842; G06F 3/0482; G06F 17/3053; G06F 17/30563; H04L 63/20
See application file for complete search history.

(56) References Cited

U.S. PATENT DOCUMENTS

| 8,671,009 | B1* | 3/2014 | Coley | G06Q 10/109 |
| | | | | 705/7.13 |
| 2002/0022551 | A1* | 2/2002 | Watterson | H04L 67/02 |
| | | | | 482/8 |
| 2008/0058773 | A1* | 3/2008 | John | G16H 50/20 |
| | | | | 604/891.1 |
| 2010/0212675 | A1* | 8/2010 | Walling | G06F 19/3418 |
| | | | | 128/898 |
| 2010/0279823 | A1* | 11/2010 | Waters | A63B 24/0006 |
| | | | | 482/8 |
| 2011/0071003 | A1* | 3/2011 | Watterson | A63B 21/005 |
| | | | | 482/8 |
| 2012/0094258 | A1* | 4/2012 | Langheier | G06F 19/3475 |
| | | | | 434/127 |

(Continued)

*Primary Examiner* — Neal Sereboff
(74) *Attorney, Agent, or Firm* — Medley, Behrens & Lewis, LLC

(57) ABSTRACT

A method includes receiving from a health care practitioner input corresponding to creation of a first health care order which includes one or more parameters associated with a health care goal for the patient, one or more parameters associated with one or more rules for communicating notifications regarding the first health care order to the first health care practitioner via the electronic health records application, and instructions for the patient for complying with the first health care order. The method further includes displaying to the patient a patient portal comprising a goals interface which displays information associated with the first health care order for the patient created by the first health care practitioner, and allowing the patient to input readings for the order. The method further includes communicating one or more notifications back to the electronic health records application based on the readings.

10 Claims, 40 Drawing Sheets

(56) References Cited

U.S. PATENT DOCUMENTS

| | | | |
|---|---|---|---|
| 2012/0289803 A1* | 11/2012 | Weinert | G06F 19/3456 600/365 |
| 2012/0323346 A1* | 12/2012 | Ashby | A63B 21/005 700/91 |
| 2013/0211858 A1* | 8/2013 | Ohnemus | G06Q 50/22 705/3 |

* cited by examiner

▽ Weight Management                                                                                                  X Take weight once a day.                Goal  [Lose ▷]  [10.0 ◁▷]  [pound(s) ▷]  in  [3 ◁▷]  [month(s) ▷]

┌─ Order Rules ─────────────────────────────────────────────────────────────────
│ ⊙ On   ○ Off    Send notification if  [7 ◁▷]  consecutive readings are missed
│
│ ⊙ On   ○ Off    Send notification if the patient does not consent to the order  [7 ◁▷]  days after it was placed
└───────────────────────────────────────────────────────────────────────────────

Patient Instructions
┌───────────────────────────────────────────────────────────────────────────────
│ Weigh yourself first thing in the morning after urinating but before eating and drinking.  Be sure to wear similar clothing and always use the same
│ scale.
└───────────────────────────────────────────────────────────────────────────────

* Initial and target weight will be established using the first reading from the patient's home scale.

*FIG. 2*

▽ Weight Management                                                                                           X Take weight once a day.                    Goal  [▽] [10.0 ◊] [pound(s) ▽]  in  [3 ◊]  [month(s) ▽]
                                                 Gain
　Order Rules                                    Lose
　⦿ On　○ Off　　Send notification if  [7 ◊] consecutive re↖missed ⦿ On　○ Off　　Send notification if the patient does not consent to the order [7 ◊] days after it was placed Patient Instructions Weigh yourself first thing in the morning after urinating but before eating and drinking.  Be sure to wear similar clothing and always use the same scale.

* Initial and target weight will be established using the first reading from the patient's home scale.

*FIG. 3*

▽ Weight Management                                                              X Take weight once a day.    Goal  [Lose ▷]  [9.9 ⬍]  [pound(s) ▷]  in  [3 ⬍]  [month(s) ▷]

── Order Rules ──

⦿ On  ○ Off    Send notification if  [7 ⬍] consecutive readings are missed

⦿ On  ○ Off    Send notification if the patient does not consent to the order [7 ⬍] days after it was placed Patient Instructions Weigh yourself first thing in the morning after urinating but before eating and drinking. Be sure to wear similar clothing and always use the same scale.

* Initial and target weight will be established using the first reading from the patient's home scale.

*FIG. 4*

Weight Management

Take weight once a day.    Goal [Lose ▽] [10.0 ⇔] [pound(s) ▽] in [3 ⇔] [month(s) ▽]

Order Rules

⦿ On   ○ Off    Send notification if [7 ⇔] consecutive readings are missed

⦿ On   ○ Off    Send notification if the patient does not consent to the order [7 ⇔] days after it was placed

Patient Instructions

Weigh yourself first thing in the morning after urinating but before eating and drinking. Be sure to wear similar clothing and always use the same scale.

* Initial and target weight will be established using the first reading from the patient's home scale.

*FIG. 5*

▽ Weight Management                                                                                       X Take weight once a day.                      Goal [Lose ▽] [10.0 ◁▷] [pound(s) ▽] in [3 ◁▷] [month(s) ▽]

┌─ Order Rules ──────────────────────────────────────────────────────────────────┐
│ ○ On  ◉ Off      Send notification if [7 ◁▷] consecutive readings are missed    │
│                                                                                  │
│ ◉ On  ○ Off      Send notification if the patient does not consent to the order [7 ◁▷] days after it was placed │
└──────────────────────────────────────────────────────────────────────────────┘

Patient Instructions
┌──────────────────────────────────────────────────────────────────────────────┐
│ Weigh yourself first thing in the morning after urinating but before eating and drinking. Be sure to wear similar clothing and always use the same │
│ scale.                                                                           │
└──────────────────────────────────────────────────────────────────────────────┘

* Initial and target weight will be established using the first reading from the patient's home scale.

*FIG. 6*

▽ Weight Management                                                                    X Take weight once a day.           Goal  [Lose ▽]  [10.0 ◁▷]  pound(s) ▽  in  [3 ◁▷]  month(s) ▽

Order Rules

○ On  ⊙ Off    Send notification if [7 ◁▷] consecutive readings are missed

⊙ On  ○ Off    Send notification if the patient does not consent to the order [6 ◁▷🖑] days after it was placed Patient Instructions Weigh yourself first thing in the morning after urinating but before eating and drinking. Be sure to wear similar clothing and always use the same scale.

* Initial and target weight will be established using the first reading from the patient's home scale.

*FIG. 7*

▽ Weight Management                                                                                    X Take weight once a day.                Goal [Lose ▷]   [10.0 ◁▷] [pound(s) ▷] in [3 ◁▷] [month(s) ▷]

Order Rules

○ On  ⦿ Off    Send notification if [7 ◁▷] consecutive readings are missed

⦿ On  ○ Off    Send notification if the patient does not consent to the order [6 ◁▷] days after it was placed Patient Instructions

| Weigh yourself first thing in the morning after urinating but before eating and drinking. Be sure to wear similar clothing and always use the same scale. |

* Initial and target weight will be established using the first reading from the patient's home scale.

*FIG. 8A*

▽ Weight Management                                                                                        X Take weight once a day.                         Goal  [Lose ▷]  [10.0 ◁▷]  [pound(s) ▷]  in  [3 ◁▷]  [month(s) ▷]

┌ Order Rules ──────────────────────────────────────────────────────────────┐
│                                                                            │
│ ○ On  ⦿ Off    Send notification if  [7 ◁▷] consecutive readings are missed │
│                                                                            │
│ ⦿ On  ○ Off    Send notification if the patient does not consent to the order [6 ◁▷] days after it was placed │
└────────────────────────────────────────────────────────────────────────────┘

Patient Instructions

┌────────────────────────────────────────────────────────────────────────────┐
│ Weigh yourself first thing in the morning after urinating but before eating│drinking. Be sure to wear similar clothing and always use the same scale. │
└────────────────────────────────────────────────────────────────────────────┘

* Initial and target weight will be established using the first reading from the patient's home scale.

*FIG. 8B*

▽ Weight Management                                                                                           X Take weight once a day.                           Goal  [Lose ▷] [10.0 ◁▷] [pound(s) ▷] in [3 ◁▷] [month(s) ▷]

─ Order Rules ──────────────────────────────────────────────────────────────
○ On  ● Off    Send notification if [7 ◁▷] consecutive readings are missed ● On  ○ Off    Send notification if the patient does not consent to the order [6 ◁▷] days after it was placed Patient Instructions Weigh yourself first thing in the morning after urinating but before eating or drinking. Be sure to wear similar clothing and always use the same scale.

* Initial and target weight will be established using the first reading from the patient's home scale.

*FIG. 8C*

▽ Weight Management                                                                                          x Take weight once a day.                Goal  [Lose ▽]  [10.0 ◁▷]  [pound(s) ▽]  in  [3 ◁▷]  [month(s) ▷]

┌─ Order Rules ─────────────────────────────────────────────────────────────────────
│ ○ On  ⦿ Off    Send notification if  [7 ◁▷]  consecutive readings are missed
│
│ ⦿ On  ○ Off    Send notification if the patient does not consent to the order  [6 ◁▷]  days after it was placed ┌─ Notifications ───────────────────────────────────────────────────────────────────
│ Send notifications to:   ☑ Myself                    ☑ Other Users          ☐ User Group(s)
│                                                      [⊕ ⊖ ≡]                [⊕ ⊖ ≡]
│                          ☐ Email: [          ]       Wright, James D.
│                                                      Tillman, Chad D.
│                          ☐ Text:  [          ]       Mattei, Peter J.
│                                                      Clark, Chris C.

Patient Instructions

Weigh yourself first thing in the morning after urinating but before eating or drinking. Be sure to wear similar clothing and always use the same
scale.

* Initial and target weight will be established using the first reading from the patient's home scale.

*FIG. 9*

▽ Monitor Weight                                                                                                    X Take weight once a day for [60 ⇳] [day(s) ▷]

Order Rules

○ On  ⦿ Off    Send notification if weight [increases ▷] at least [3.0 ⇳] [pound(s) ▷] in [1 ⇳] [day(s) ▷]

○ On  ⦿ Off    Send notification if weight [increases or decreases ▷] at least [5.0 ⇳] [pound(s) ▷] in
                [1 ⇳] [week(s) ▷]

⦿ On  ○ Off    Send notification if [3 ⇳] consecutive readings are missed

⦿ On  ○ Off    Send notification if the patient does not consent to the order [7 ⇳] days after it was placed Patient Instructions Weigh yourself first thing in the morning after urinating but before eating and drinking. Be sure to wear similar clothing and always use the same scale.

* Baseline weight will be established using the first reading from the patient's home scale.

*FIG. 11A*

▽ Monitor Weight

Take weight once a day for [60 ◁▷] day(s) [▷]

Order Rules

○ On  ◉ Off   Send notification if weight [increases ▷] at least [3.0 ◁▷] pound(s) [▷] in [1 ◁▷] day(s) [▷]

○ On  ◉ Off   Send notification if weight
                           ┌─────────────────────────┐
                           │ increases               │
[1 ◁▷] week(s) [▷]           │ decreases           │ at least [5.0 ◁▷] pound(s) [▷] in [1 ◁▷] pound(s) [▷]
                           │ increases or decreases  │
                           └─────────────────────────┘

◉ On  ○ Off   Send notification if [3 ◁▷]

◉ On  ○ Off   Send notification if the patient does not consent to the order [7 ◁▷] days after it was placed

Patient Instructions

Weigh yourself first thing in the morning after urinating but before eating and drinking. Be sure to wear similar clothing and always use the same scale.

* Baseline weight will be established using the first reading from the patient's home scale.

*FIG. 11B*

▽ Monitor Weight                                                                                    X Take weight once a day for [60 ◁▷] [day(s) ▷]

┌─ Order Rules ─────────────────────────────────────────────────────────────────
│
│  ○ On  ⦿ Off    Send notification if weight  [increases ▷]  at least  [3.0 ◁▷]  [pound(s) ▷]  in  [1 ◁▷]  [day(s) ▷]
│
│  ○ On  ⦿ Off    Send notification if weight  [increases or decreases ▷]  at least  [5.0 ◁▷]  [pound(s) ▷]  in
│                 [1 ◁▷]  [week(s) ▷]
│
│  ⦿ On  ○ Off    Send notification if  [3 ◁▷]  consecutive readings are missed
│
│  ⦿ On  ○ Off    Send notification if the patient does not consent to the order  [7 ◁▷]  days after it was placed
│
│  Add a rule Patient Instructions ┌──────────────────────────────────────────────────────────────────────────────┐
│ Weigh yourself first thing in the morning after urinating but before eating and drinking. Be sure to wear similar clothing and always use the same │
│ scale.                                                                       │
└──────────────────────────────────────────────────────────────────────────────┘

* Baseline weight will be established using the first reading from the patient's home scale.

*FIG. 12*

▽ Monitor Weight                                                                            X Take weight once a day for [60] ◁▷ [day(s)] ▷

Order Rules

○ On  ◉ Off    Send notificati[on]  ▷  in  ▷  [day(s)] ▷

○ On  ◉ Off    Send notificati[on]  ┌─────────────────────────────────┐
                                    │         Add Rule            │
                                    │                                 │
                                    │  ◉ Weight Change Notification Rule │
              [1] ◁▷                │                                 │
◉ On  ○ Off    Send notificati[on]  │  ○ Missed Reading Notification Rule │
                                    │                                 │
◉ On  ○ Off    Send notificati[on]  │  ○ Failure to Consent Notification Rule │
                                    │                                 │
<u>Add a rule</u>                          │  ○ Custom Rule                  │
                                    │                                 │
                                    │    ┌────────┐    ┌─────┐        │
                                    │    │ Cancel │    │ Add │        │
                                    │    └────────┘    └─────┘        │
                                    └─────────────────────────────────┘
                                          [pound(s)] ▷ it was placed

Patient Instructions

Weigh yourself first thing in the morning after urinating but before eating and drinking. Be sure to wear similar clothing and always use the same scale.

* Baseline weight will be established using the first reading from the patient's home scale.

*FIG. 13*

▽ Monitor Weight                                                                                                               X Take weight once a day for [60 ◁▷] [day(s) ▷]

─ Order Rules ────────────────────────────────────────────────────

○ On  ⦿ Off   Send notification if weight [increases ▷] at least [3.0 ◁▷] [pound(s) ▷] in [1 ◁▷] [day(s) ▷]

○ On  ⦿ Off   Send notification if weight [increases or decreases ▷] at least [5.0 ◁▷] [pound(s) ▷] in
              [1 ◁▷] [week(s) ▷]

○ On  ⦿ Off   Send notification if weight [increases or decreases ▷] at least [10.0 ◁▷] [pound(s) ▷] in
              [1 ◁▷] [month(s) ▷]

⦿ On  ○ Off   Send notification if [3 ◁▷] consecutive readings are missed

⦿ On  ○ Off   Send notification if the patient does not consent to the order [7 ◁▷] days after it was placed Add a rule Patient Instructions Weigh yourself first thing in the morning after urinating but before eating and drinking. Be sure to wear similar clothing and always use the same scale.

* Baseline weight will be established using the first reading from the patient's home scale.

*FIG. 14*

▽ Monitor Weight

Take weight once a day for [ 60 ◁▷ ] [ day(s) ▷ ]

Order Rules

○ On  ⦿ Off   Send notification if weight [ increases ▷ ] at least [ 3.0 ◁▷ ] [ pound(s) ▷ ] in [ 1 ◁▷ ] [ day(s) ▷ ] ⊗

○ On  ⦿ Off   Send notification if weight [ increases or decreases ▷ ] at least [ 5.0 ◁▷ ] [ pound(s) ▷ ] in
               [ 1 ◁▷ ] [ week(s) ▷ ] ⊗

○ On  ⦿ Off   Send notification if weight [ increases or decreases ▷ ] at least [ 10.0 ◁▷ ] [ pound(s) ▷ ] in
               [ 1 ◁▷ ] [ month(s) ▷ ] ⊗

⦿ On  ○ Off   Send notification if [ 3 ◁▷ ] consecutive readings are missed ⊗

⦿ On  ○ Off   Send notification if the patient does not consent to the order [ 7 ◁▷ ] days after it was placed ⊗

<u>Add a rule</u>

Patient Instructions

Weigh yourself first thing in the morning after urinating but before eating and drinking. Be sure to wear similar clothing and always use the same scale.

\* Baseline weight will be established using the first reading from the patient's home scale.

*FIG. 15*

▽ Monitor Blood Pressure                                                                                          X Take blood pressure [ 3 ◁▷ ] times [ a day ◁▷ ] for [ 30 ◁▷ ] [ days ◁▷ ]   Goal [ < ◁▷ ] [ 140 ◁▷ ] / [ 90 ◁▷ ] mmHG ── Order Rules ──

● On   ○ Off    Send notification if systolic BP is >= [ 165 ◁▷ ] or <= [ 85 ◁▷ ] mmHG ○ On   ● Off    Send notification if diastolic BP is >= [ 100 ◁▷ ] or <= [ 50 ◁▷ ] mmHG ● On   ○ Off    Send notification if no readings are taken over a [ 3 ◁▷ ] day period ● On   ○ Off    Send notification if the patient does not consent to the order [ 7 ◁▷ ] days after it was placed                        mmHG Patient Instructions Rest in a chair for 5 to 10 minutes with your arm at heart level before taking your blood pressure. Sit up straight with your legs uncrossed. Take it at different times during the day. Make sure to keep track of what you were doing before taking it. This can be entered into the comments field for the blood pressure reading.

*FIG. 16*

▽ Monitor Blood Glucose

Take your blood glucose reading [ 7 ◁▷ ] times a [ day ▷ ] for [ 2 ◁▷ ] [ month(s) ▷ ]

Measurement Times
- ☐ if experiencing symptoms
- ☐ before breakfast/fasting
- ☑ before meals
- ☑ 1 to 2 hours after meals
- ☑ before activity
- ☐ after activity
- ☐ bedtime/overnight

Target Ranges

[ 70 ◁▷ ] to [ 130 ◁▷ ] mg/dL   before meals   ⊗

[ 60 ◁▷ ] to [ 179 ◁▷ ] mg/dL   1 to 2 hours after meals, bedtime/overnight   ⊗

Add a target range

Order Rules

- ⦿ On   ○ Off   Send notification if adherence is less than [ 60 % ◁▷ ] over a [ 5 ◁▷ ] day period
- ⦿ On   ○ Off   Send notification if any reading is at least [ 100 ◁▷ ] mg/dL outside a target range
- ⦿ On   ○ Off   Send notification if any reading is <= [ 20 ◁▷ ] or >= [ 600 ◁▷ ] mg/dL
- ⦿ On   ○ Off   Send notification if the patient does not consent to the order [ 7 ◁▷ ] day(s) after it was placed Patient Instructions Please be sure to enter what you were doing when the measurement was taken (e.g. after breakfast) so that it can be properly evaluated against your target ranges.

| Goals | | | X |
|---|---|---|---|
| Your provider has set the following goals for you. FollowMyHealth makes it easy to capture relevant information to track your progress toward each goal. By accepting these goals you are authorizing the release of related information to your health care team. This information can be sued by your care to to assist you in reaching these goals. | | | |
| Goal | Requested By | Accept | Decline |
| Lose 15 pounds in 4 months | John Smith – Jardogs Demo Clinic | O | O |
| Maintain a blood pressure less than 150/95 mmHg for 30 days | John Smith – Jardogs Demo Clinic | O | O |
| Monitor Blood Glucose 6 times a day for 60 days | John Smith – Jardogs Demo Clinic | O | O |
| Monitor Weight for 60 days | John Smith – Jardogs Demo Clinic | O | O |
| | | Continue | Cancel |

*FIG. 20*

Goal Release of Information Authorization

Patient:
Zztest, Jardogs99

Date Of Birth:
12/15/1947

Written By:
Not Listed

Contents:

Your provider has set the following goals for you. FollowMyHealth makes it easy to capture relevant information to track your progress towards each goal. By accepting these goals you are authorizing the release of related information to your health care team. This information can be used by your care team to assist you in reaching these goals Accepted Goals:
Monitor Weight for 60 days Declined Goals:
Maintain a blood pressure less than 140/90 mmHg for 30 days.

Requested By:
Test Provider – Test Organization

Signed on 1/3/2014 by zztest, Jardogs99

[Email]  [Print]  [Fax]

*FIG. 21*

Decline Goal

Goal: Lose 10 pounds in 3 months

Requested By: John Smith – Jardogs Demo Clinic

You are declining this goal. Information related to this goal will on longer be shared with your care team.

Your care team will be notified of this change

[ Decline Goal ]   [ Cancel ]

*FIG. 22*

Add Vital

Type:
[ Weight ▽ ]

Date Taken:
[ 09/13/2013  3:02 PM ]

Value:
[ 178.0 ]  [ pound(s) ▽ ]

Comments:
This was not taken first thing in the morning. I was so excited to get started that I weighed mayself at 3 in the afternoon after getting home from the clinic.

[ Save ]  [ Cancel ]

Lose 10.0 pounds in 3 months | Start: 09/13/2013 | End: 12/13/2013

Weigh yourself everyday first thing in the morning after urinating but before eating or drinking. Be sure to wear similar clothing and always use the same scale.

Last Reading: 174.8 lbs    26.7 BMI    Target Weight: 168.0 lbs    Progress: -3.2 lbs in 28 days    32%    Add a Reading

| Date | Δ Weight | Comments | Source | Options |
|---|---|---|---|---|
| 10/15/13 | 174.8 lbs | | Withings Scale | ✎ ⊗ |
| 10/14/13 | 175.8 lbs | | Withings Scale | ✎ ⊗ |
| 10/13/13 | 175.9 lbs | | Withings Scale | ✎ ⊗ |
| 10/11/13 | 176.2 lbs | | Withings Scale | ✎ ⊗ |
| 10/10/13 | 179.5 lbs | this was taken at 9 pm because I forgot. | Withings Scale | ✎ ⊗ |
| 10/09/13 | 176.5 lbs | | Withings Scale | ✎ ⊗ |
| 10/08/13 | 176.7 lbs | I was bad yesterday. It was my my wife's birthday and I took her out for a fancy dinner. | Withings Scale | ✎ ⊗ |
| 10/07/13 | 176.4 lbs | | Withings Scale | ✎ ⊗ |

** Only data that you enter into FollowMyHealth manually or automatically using a Withings scale is used for this order. This is to prevent the results from being measurements from other scales such as measurements taken during a visit to your health care provider.

Decline this Goal                                                                                    Connect to a Withings Scale

FIG. 25

Confirm Delete

You are choosing to delete information from your FollowMyHealth Universal Health Record. Please note that these changes will not take effect in your Healthcare Provider's EMR. To make permanent changes to your legal health record, please contact your Healthcare Provider.

☐ Do not show this message again

[ Yes ]  [ No ]

*FIG. 27*

Monitor Weight for 60 days  Start: 09/13/2013  End: 11/12/2013

Weigh yourself everyday first thing in the morning after urinating but before eating or drinking. Be sure to wear similar clothing and always use the same scale.
Watch for an increase of at least 3 pounds in 1 day or at least 5 pounds in 1 week.

Add a Reading

| Date | △ Weight | Comments | Source | Options |
|------|----------|----------|--------|---------|
| 10/15/13 | 174.8 lbs | | Withings Scale | ✏ ⊗ |
| 10/14/13 | 175.8 lbs | | Withings Scale | ✏ ⊗ |
| 10/13/13 | 175.9 lbs | | Withings Scale | ✏ ⊗ |
| 10/11/13 | 176.2 lbs | 179 lbs   27.2 BMI   09/27/13  Weight increase greater than 3 pounds in 1 day. | Withings Scale | ✏ ⊗ |
| 10/10/13 | 179.5 lbs | this was taken at 9 pm because I forgot. | Withings Scale | ✏ ⊗ |
| 10/09/13 | 176.4 lbs | | Withings Scale | ✏ ⊗ |
| 10/08/13 | 176.7 lbs | I was bad yesterday. It was my wife's birthday and I took her out for a fancy dinner. | Withings Scale | ✏ ⊗ |
| 10/07/13 | 176.4 lbs | | Withings Scale | ✏ ⊗ |

\*\* Only data that you enter into FollowMyHealth manually or automatically using a Withings scale is use for this order. This is to prevent the results from being measurements from other scales such as measurements taken during a visit to your health care provider.
Decline this Goal                                                                                                          Connect to a Withings Scale

FIG. 28

Add Blood Glucose

Name: Glucose BldC - mCnc

Date Taken: 09/13/2013 11:45 AM

Glucose: 157 mg/dL

Tag: 1 to 2 hours after meals
- Before meals
- 1 to 2 hours after meals
- Before breakfast/fasting
- At bedtime/overnight
- Before activity
- After activity Comments: This can only be gluc[ose]. These are the only tw[o]. We use fas[ting] breakfast/fasting and pick anything else.

Save  Cancel

*FIG. 31*

| Monitor Blood Glucose 6 times a day for 60 days | | Start: 09/13/2013 | | End: 11/12/2013 |
|---|---|---|---|---|
| Your provider has requested that you monitor your blood glucose levels before and 1 to 2 hours after meals. The goal is to keep the readings within the following target ranges: | | | | |
| Before meals | | | | |
| <70 low | 70 to 130 normal | | >130 high | |
| 1 to 2 hours after meals | | | | |
| <60 low | 60 to 179 normal | | >179 high | |
| Please be sure to enter what you were doing when the measurement was taken (e.g. after breakfast) so that it can be properly evaluated against your target ranges. | | | | Add a Reading |

| Date | Glucose | Tag | Comments | Source | Options |
|---|---|---|---|---|---|
| 09/13/2013 11:45 AM | 157 mg/dL | before breakfast/fasting | These are the patients comments and they wrap if they need to in order to fit in the column. | Telcare BGM | ✎ ⊗ |

Decline this goal.

Connect to a Telcare Blood Glucose Meter

*FIG. 32*

Monitor Blood Glucose 6 times a day for 60 days

Start: 09/13/2013    End: 11/12/2013

Your provider has requested that you monitor your blood glucose levels before and 1 to 2 hours after meals. The goal is to keep the readings within the following target ranges:

Before meals

| <70 | 70 to 130 | >130 |
|-----|-----------|------|
| low | normal    | high |

1 to 2 hours after meals

| <60 | 60 to 179 | >179 |
|-----|-----------|------|
| low | normal    | high |

Please be sure to enter what you were doing when the measurement was taken (e.g. after breakfast) so that it can be properly evaluated against your target ranges.

Add a Reading

| Date | Glucose | Tag | Comments | Source | Options |
|------|---------|-----|----------|--------|---------|
| 10/13/13 11:31 AM | 174 mg/dL | 1 to 2 hours after a meal | | Telcare BGM | |
| 9/29/13 10:54 PM | 224 mg/dL | 1 to 2 hours after a meal | | Telcare BGM | |
| 9/24/13 10:46 AM | 122 mg/dL | 1 to 2 hours after a meal | | Telcare BGM | |
| 9/24/13 07:14 AM | 62 mg/dL | 185 mg/dL  1 to 2 hours after a meal | 09/18/13 3:21 PM | Telcare BGM | |
| 9/18/13 08:54 PM | 158 mg/dL | This reading is outside the target range of 60 to 175 mg/dL 1 to 2 hours after a meal. | | Telcare BGM | |
| 9/18/13 07:11 PM | 77 mg/dL | 1 to 2 hours after a meal | | Telcare BGM | |
| 9/18/13 03:21 PM | 185 mg/dL | before breakfast/fasting | These are the patients comments and they wrap if they need to in order to fit in the column. | Telcare BGM | |
| 9/13/13 11:45 AM | 157 mg/dL | | | Telcare BGM | |

Decline this Goal    Connect to a Telcare Blood Glucose Meter

*FIG. 33*

| | |
|---|---|
| Maintain a blood pressure less than 150 / 95 mmHg for 30 days | |
| | Your provider has requested that you monitor your blood pressure. The goal is to keep it less than 50 / 95 mmHg. |
| | Take your blood pressure 3 times a day. Rest in a chair for 5 to 10 minutes with your arm at heart level before taking your blood pressure. Sit up straight with your legs uncrossed. Take it a different times during the day. Make sure to keep track of what you were doing before taking it. This can be entered into the comments field for the blood pressure reading in FollowMyHealth. |
| | To begin  enter your blood pressure  or  connect to a Withings Blood Pressure Monitor to automatically have your blood pressure added to FollowMyHealth. You may also decline this goal. |

*FIG. 34*

Add Vital  ✕

Type: [ Blood Pressure ▽ ]

Date Taken: [ 09/13/2013   11:45 AM ] 🔳

Value: [ 145/101 ]

Comments: [                    ]

[ Save ]
[ Cancel ]

*FIG. 35*

Maintain a blood pressure less than 150 / 95 mmHG for 30 days  Start: 09/13/2013    End: 10/13/2013

Take your blood pressure 3 times a day. Rest in a chair for 5 to 10 minutes with your arm at heart level before taking your blood pressure. Sit up straight with your legs uncrossed. Take it a different times during the day. Make sure to keep track of what you were doing before taking it. This can be entered into the comments field for the blood pressure reading in FollowMyHealth.

Add a Reading

| Date | △Blood Pressure | Comments | Source | Options |
|---|---|---|---|---|
| 09/13/2013 11:45 AM | 145/101 mmHG | | Withings BP | ✎ ⊗ |

Decline this goal.    Connect to a Telcare Blood Glucose Meter

*FIG. 36*

Maintain a blood pressure less than 150 / 95 mmHG for 30 days          Start: 09/13/2013          End: 10/13/2013

Take your blood pressure 3 times a day. Rest in a chair for 5 to 10 minutes with your arm at heart level before taking your blood pressure. Sit up straight with your legs uncrossed. Take it a different times during the day. Make sure to keep track of what you were doing before taking it. This can be entered into the comments field for the blood pressure reading in FollowMyHealth.

Add a Reading

| Date | △ | Blood Pressure | Comments | Source | Options |
|---|---|---|---|---|---|
| 10/16/13 01:34 PM | | 129/89 mmHg | | Withings BP | 📝 ⊗ |
| 10/16/13 06:35 AM | | 152/95 mmHg | | Withings BP | 📝 ⊗ |
| 10/15/13 10:42 PM | | 146/92 mmHg | 157/102 mmHg        09/27/13   4:21 PM | Withings BP | 📝 ⊗ |
| 10/15/13 08:30 AM | | 132/89 mmHg | Blood pressure exceeds the goal of less than 150/95 | Jardogs Clinic | 📝 ⊗ |
| 10/14/13 04:21 PM | | 157/102 mmHg | | Withings BP | 📝 ⊗ |
| 10/14/13 07:23 AM | | 137/86 mmHg | | Patient Entered | 📝 ⊗ |
| 10/13/13 11:38 PM | | 140/88 mmHg | I think this is a little high. I was doing some work in the garage before I took it. I did not rest very long before taking it. | Withings BP | 📝 ⊗ |
| 10/13/13 11:41 AM | | 148/95 mmHg | | Withings BP | 📝 ⊗ |

Decline this Goal                                           Connect to a Withings Blood Pressure Monitor

*FIG. 37*

FACILITATING PATIENT MONITORING

CROSS-REFERENCE TO RELATED APPLICATION

The present application is a U.S. nonprovisional patent application of, and claims priority under 35 U.S.C. § 119(e) to, U.S. provisional patent application Ser. No. 61/943,375, filed Feb. 22, 2014, and U.S. provisional patent application Ser. No. 61/943,397, filed Feb. 23, 2014. Each of these provisional patent applications is hereby incorporated herein by reference. The present application further hereby incorporates herein by reference the entire disclosure of Exhibit 1 attached hereto.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to managing the care of large populations of patients.

Conventionally, it is common to hire large numbers of nurses or care coordinators to manage patients and their care plans (which include, for example, actions required of a patient). This presents several obstacles to managing populations of patients. For example, it can be difficult to ascertain how many patients each nurse/coordinator can manage effectively. Further, it can be difficult to figure out how to handle communication with patients in an efficient way, and it can be difficult to determine how often nurses/coordinators should reach out to patients.

Needs exist for improvement in managing the care of large populations of patients. These needs, and other needs, are addressed by one or more aspects of the present invention.

SUMMARY OF THE INVENTION

The present invention includes many aspects and features. Moreover, while many aspects and features relate to, and are described in, the context of population health methodologies, the present invention is not limited to use only in this context, as will become apparent from the following summaries and detailed descriptions of aspects, features, and one or more embodiments of the present invention.

Accordingly, one aspect of the present invention relates to a method which includes receiving from a health care practitioner input corresponding to creation of a first health care order which includes one or more parameters associated with a health care goal for the patient, one or more parameters associated with one or more rules for communicating notifications regarding the first health care order to the first health care practitioner via the electronic health records application, and instructions for the patient for complying with the first health care order. The method further includes displaying to the patient a patient portal comprising a goals interface which displays information associated with the first health care order for the patient created by the first health care practitioner, and allowing the patient to input readings for the order. The method further includes communicating one or more notifications back to the electronic health records application based on the readings.

Another aspect relates to a method which includes displaying, to a first health care practitioner via a display device associated with a first electronic device, an interface of an electronic health records application; receiving, from the first health care practitioner via one or more input devices associated with the first electronic device, input corresponding to engagement with an order creation interface element of the displayed interface of the electronic health records application; displaying, to the first health care practitioner via a display device associated with the first electronic device, an order creation interface for creating a health care order configured to allow the first health care practitioner to specify one or more parameters associated with a health care goal for the patient, one or more parameters associated with one or more rules for communicating notifications regarding the health care order to the first health care practitioner via the electronic health records application, and instructions for the patient for complying with the health care order; receiving, from the first health care practitioner via one or more input devices associated with the first electronic device, input corresponding to creation of a first health care order which includes first one or more parameters associated with a first health care goal for the patient, second one or more parameters associated with one or more rules for communicating notifications regarding the first health care order to the first health care practitioner via the electronic health records application, the one or more rules including rules governing communication of a notification that the first health care order has not been accepted a first number of days after its creation, the first number of days being specified by a parameter of the second one or more parameters, communication of a notification that no reading has been input by the patient for a second number of days, the second number of days being specified by a parameter of the second one or more parameters; and first instructions for the patient for complying with the first health care order; displaying, to the patient via a display device associated with a second electronic device, an interface of a patient portal comprising a goals interface which displays information associated with the first health care order for the patient created by the first health care practitioner; receiving, from the patient via the patient portal, an indication of acceptance of the first health care order; displaying, to the patient via the patient portal, the first health care goal for the patient and the first instructions for the patient for complying with the first health care order; receiving data for one or more vital readings associated with the first health care order; automatically determining, based on the one or more vital readings, that one of the one or more rules for communicating notifications regarding the first health care order was violated; and automatically communicating, based on the determination that one of the one or more rules was violated, a notification to the first health care practitioner.

In a feature of this aspect, the first electronic device comprises a computer.

In a feature of this aspect, the first electronic device comprises a tablet.

In a feature of this aspect, the first electronic device comprises a phone.

In a feature of this aspect, the first electronic device comprises a touchscreen.

In a feature of this aspect, the first health care practitioner comprises a doctor.

In a feature of this aspect, the first health care practitioner comprises a nurse.

In a feature of this aspect, the first health care practitioner comprises a physician's assistant.

In a feature of this aspect, the first health care practitioner comprises an employee of a health care entity.

In a feature of this aspect, the health care goal for the patient comprises losing weight.

In a feature of this aspect, the health care goal for the patient comprises gaining weight.

In a feature of this aspect, receiving data for one or more vital readings associated with the first health care order comprises receiving data input by the patient via the patient portal.

In a feature of this aspect, receiving data for one or more vital readings associated with the first health care order comprises receiving data from an electronic measurement device. In accordance with one or more preferred implementations, the electronic measurement device comprises a scale. In accordance with one or more preferred implementations, the electronic measurement device comprises a Withings scale. In accordance with one or more preferred implementations, the electronic measurement device comprises a blood pressure monitor. In accordance with one or more preferred implementations, the electronic measurement device comprises a Withings blood pressure monitor. In accordance with one or more preferred implementations, the electronic measurement device comprises a blood glucose meter. In accordance with one or more preferred implementations, the electronic measurement device comprises a Telcare blood glucose meter.

In a feature of this aspect, automatically determining, based on the one or more vital readings, that one of the one or more rules for communicating notifications regarding the first health care order was violated comprises automatically determining that a patient's weight increased by an amount specified by a parameter of the second set of parameters over a time period specified by a parameter of the second set of parameters.

In a feature of this aspect, automatically determining, based on the one or more vital readings, that one of the one or more rules for communicating notifications regarding the first health care order was violated comprises automatically determining that a patient's weight decreased by an amount specified by a parameter of the second set of parameters over a time period specified by a parameter of the second set of parameters.

In a feature of this aspect, automatically determining, based on the one or more vital readings, that one of the one or more rules for communicating notifications regarding the first health care order was violated comprises automatically determining that a patient's weight increased or decreased by an amount specified by a parameter of the second set of parameters over a time period specified by a parameter of the second set of parameters.

In a feature of this aspect, automatically determining, based on the one or more vital readings, that one of the one or more rules for communicating notifications regarding the first health care order was violated comprises automatically determining that a patient's systolic blood pressure is greater than or equal to a value specified by a parameter of the second set of parameters.

In a feature of this aspect, automatically determining, based on the one or more vital readings, that one of the one or more rules for communicating notifications regarding the first health care order was violated comprises automatically determining that a patient's systolic blood pressure is greater than a value specified by a parameter of the second set of parameters.

In a feature of this aspect, automatically determining, based on the one or more vital readings, that one of the one or more rules for communicating notifications regarding the first health care order was violated comprises automatically determining that a patient's systolic blood pressure is less than or equal to a value specified by a parameter of the second set of parameters.

In a feature of this aspect, automatically determining, based on the one or more vital readings, that one of the one or more rules for communicating notifications regarding the first health care order was violated comprises automatically determining that a patient's systolic blood pressure is less than a value specified by a parameter of the second set of parameters.

In a feature of this aspect, automatically determining, based on the one or more vital readings, that one of the one or more rules for communicating notifications regarding the first health care order was violated comprises automatically determining that a patient's diastolic blood pressure is greater than or equal to a value specified by a parameter of the second set of parameters.

In a feature of this aspect, automatically determining, based on the one or more vital readings, that one of the one or more rules for communicating notifications regarding the first health care order was violated comprises automatically determining that a patient's diastolic blood pressure is greater than a value specified by a parameter of the second set of parameters.

In a feature of this aspect, automatically determining, based on the one or more vital readings, that one of the one or more rules for communicating notifications regarding the first health care order was violated comprises automatically determining that a patient's diastolic blood pressure is less than or equal to a value specified by a parameter of the second set of parameters.

In a feature of this aspect, automatically determining, based on the one or more vital readings, that one of the one or more rules for communicating notifications regarding the first health care order was violated comprises automatically determining that a patient's diastolic blood pressure is less than a value specified by a parameter of the second set of parameters.

In a feature of this aspect, automatically determining, based on the one or more vital readings, that one of the one or more rules for communicating notifications regarding the first health care order was violated comprises automatically determining that a vital reading is outside of a target range by a value specified by a parameter of the second set of parameters.

In a feature of this aspect, automatically determining, based on the one or more vital readings, that one of the one or more rules for communicating notifications regarding the first health care order was violated comprises automatically determining that a delta between two vital readings is greater than a value specified by a parameter of the second set of parameters.

In a feature of this aspect, automatically determining, based on the one or more vital readings, that one of the one or more rules for communicating notifications regarding the first health care order was violated comprises automatically determining that a delta between two vital readings is greater than or equal to a value specified by a parameter of the second set of parameters.

In a feature of this aspect, automatically determining, based on the one or more vital readings, that one of the one or more rules for communicating notifications regarding the first health care order was violated comprises automatically determining that a vital reading is greater than a value specified by a parameter of the second set of parameters.

In a feature of this aspect, automatically determining, based on the one or more vital readings, that one of the one or more rules for communicating notifications regarding the first health care order was violated comprises automatically determining that a vital reading is greater than or equal to a value specified by a parameter of the second set of parameters.

In a feature of this aspect, automatically determining, based on the one or more vital readings, that one of the one or more rules for communicating notifications regarding the first health care order was violated comprises automatically determining that a vital reading is less than a value specified by a parameter of the second set of parameters.

In a feature of this aspect, automatically determining, based on the one or more vital readings, that one of the one or more rules for communicating notifications regarding the first health care order was violated comprises automatically determining that a vital reading is less than or equal to a value specified by a parameter of the second set of parameters.

In a feature of this aspect, automatically determining, based on the one or more vital readings, that one of the one or more rules for communicating notifications regarding the first health care order was violated comprises automatically determining that a blood glucose vital reading is outside of a target range.

In a feature of this aspect, automatically determining, based on the one or more vital readings, that one of the one or more rules for communicating notifications regarding the first health care order was violated comprises automatically determining that a vital reading is outside of a target range for a measurement time associated with that vital reading by a value specified by a parameter of the second set of parameters which is associated with that measurement time. In accordance with one or more preferred implementations, the measurement time is before meals. In accordance with one or more preferred implementations, the measurement time is 1 to 2 hours after meals. In accordance with one or more preferred implementations, the measurement time is before activity. In accordance with one or more preferred implementations, the measurement time is after activity. In accordance with one or more preferred implementations, the measurement time is bedtime. In accordance with one or more preferred implementations, the measurement time is overnight. In accordance with one or more preferred implementations, the measurement time is before breakfast/fasting.

Another aspect relates to a method which includes displaying, to a first health care practitioner via a display device associated with a first electronic device, an order creation interface for creating a health care order configured to allow the first health care practitioner to specify one or more parameters associated with one or more rules for communicating notifications regarding the health care order to the first health care practitioner via the electronic health records application, and instructions for the patient for complying with the health care order; receiving, from the first health care practitioner via one or more input devices associated with the first electronic device, input corresponding to creation of a first health care order which includes a first set of one or more parameters associated with one or more rules for communicating notifications regarding the first health care order to the first health care practitioner via the electronic health records application, the one or more rules including rules governing communication of a notification that the first health care order has not been accepted a first number of days after its creation, the first number of days being specified by a parameter of the second one or more parameters, communication of a notification that no reading has been input by the patient for a second number of days, the second number of days being specified by a parameter of the second one or more parameters; and first instructions for the patient for complying with the first health care order; displaying, to the patient via a display device associated with a second electronic device, an interface of a patient portal comprising a goals interface which displays information associated with the first health care order for the patient created by the first health care practitioner; displaying, to the patient via the patient portal, the first instructions for the patient for complying with the first health care order; receiving data for one or more vital readings associated with the first health care order; automatically determining, based on the one or more vital readings, that one of the one or more rules for communicating notifications regarding the first health care order was violated; and automatically communicating, based on the determination that one of the one or more rules was violated, a notification to the first health care practitioner.

Another aspect relates to a method which includes displaying, to a first health care practitioner via a display device associated with a first electronic device, an order creation interface for creating a health care order configured to allow the first health care practitioner to specify one or more parameters associated with one or more rules for communicating notifications regarding the health care order to the first health care practitioner via the electronic health records application, and instructions for the patient for complying with the health care order; receiving, from the first health care practitioner via one or more input devices associated with the first electronic device, input corresponding to creation of a first health care order which includes a first set of one or more parameters associated with one or more rules for communicating notifications regarding the first health care order to the first health care practitioner via the electronic health records application, the one or more rules including rules governing communication of a notification that the first health care order has not been accepted a first number of days after its creation, the first number of days being specified by a parameter of the second one or more parameters, communication of a notification that no reading has been input by the patient for a second number of days, the second number of days being specified by a parameter of the second one or more parameters; and first instructions for the patient for complying with the first health care order; receiving, from the patient via the patient portal, an indication of acceptance of the first health care order; automatically determining, after a first period of time has passed without any reading data having been input for the first health care order, that one of the rules of the first health care order has been violated because the first period of time exceeds a value specified by one of the parameters of the first set of one or more parameters; automatically communicating, based on the determination that one of the rules of the first health care order was violated, a notification to the first health care practitioner.

In a feature of this aspect, the method further comprises determining that a notification has not been sent out in connection with the first period of time having passed without any reading data having been input.

In a feature of this aspect, the method further comprises determining that a notification sent out in connection with the first period of time having passed without any reading data having been input was last sent out a certain number of days ago which exceeds the value specified by one of the parameters of the first set of one or more parameters.

Another aspect relates to a method which includes displaying, to a first health care practitioner via a display device associated with a first electronic device, an order creation interface for creating a health care order configured to allow the first health care practitioner to specify one or more parameters associated with one or more rules for communicating notifications regarding the health care order to the first health care practitioner via the electronic health records application, and instructions for the patient for complying with the health care order; receiving, from the first health care practitioner via one or more input devices associated with the first electronic device, input corresponding to creation of a first health care order which includes a first set of one or more parameters associated with one or more rules for communicating notifications regarding the first health care order to the first health care practitioner via the electronic health records application, the one or more rules including rules governing communication of a notification that the first health care order has not been accepted a first number of days after its creation, the first number of days being specified by a parameter of the second one or more parameters, communication of a notification that no reading has been input by the patient for a second number of days, the second number of days being specified by a parameter of the second one or more parameters; and first instructions for the patient for complying with the first health care order; automatically determining, after a first period of time has passed without any acceptance of the first health care order having been received, that one of the rules of the first health care order has been violated because the first period of time exceeds a value specified by one of the parameters of the first set of one or more parameters; automatically communicating, based on the determination that one of the rules of the first health care order was violated, a notification to the first health care practitioner.

In a feature of this aspect, the method further comprises determining that a notification has not been sent out in connection with the first period of time having passed without any acceptance having been received.

In a feature of this aspect, the method further comprises determining that a notification sent out in connection with the first period of time having passed without any acceptance having been received was last sent out a certain number of days ago which exceeds the value specified by one of the parameters of the first set of one or more parameters.

Another aspect relates to a method which includes receiving, from a first health care practitioner via one or more input devices associated with a first electronic device, input corresponding to creation of a first health care order which includes a first set of one or more parameters associated with one or more rules for communicating notifications regarding the first health care order to the first health care practitioner via the electronic health records application, the one or more rules including rules governing communication of a notification that the first health care order has not been accepted a first number of days after its creation, the first number of days being specified by a parameter of the second one or more parameters, communication of a notification that no reading has been input by the patient for a second number of days, the second number of days being specified by a parameter of the second one or more parameters; displaying, to the patient via a display device associated with a second electronic device, an interface of a patient portal comprising a goals interface which displays information associated with the first health care order for the patient created by the first health care practitioner; receiving data for one or more vital readings associated with the first health care order; automatically determining, based on the one or more vital readings, that one of the one or more rules for communicating notifications regarding the first health care order was violated; and automatically communicating, based on the determination that one of the one or more rules was violated, a notification to the first health care practitioner.

Another aspect relates to a method which includes receiving, from a first health care practitioner via one or more input devices associated with a first electronic device, input corresponding to creation of a first health care order which includes a first set of one or more parameters associated with one or more rules for communicating notifications regarding the first health care order to the first health care practitioner via the electronic health records application, the one or more rules including rules governing communication of a notification that the first health care order has not been accepted a first number of days after its creation, the first number of days being specified by a parameter of the second one or more parameters, communication of a notification that no reading has been input by the patient for a second number of days, the second number of days being specified by a parameter of the second one or more parameters; displaying, to the patient via a display device associated with a second electronic device, an interface of a patient portal comprising a goals interface which displays information associated with the first health care order for the patient created by the first health care practitioner; automatically determining that one of the one or more rules for communicating notifications regarding the first health care order was violated; and automatically communicating, based on the determination that one of the one or more rules was violated, a notification to the first health care practitioner.

Another aspect relates to a method which includes displaying, to a first health care practitioner via a display device associated with a first electronic device, an interface of an electronic health records application; receiving, from the first health care practitioner via one or more input devices associated with the first electronic device, input corresponding to engagement with an order creation interface element of the displayed interface of the electronic health records application; displaying, to the first health care practitioner via a display device associated with the first electronic device, an order creation interface for creating a health care order configured to allow the first health care practitioner to specify one or more parameters associated with a health care goal for the patient, one or more parameters associated with one or more rules for communicating notifications regarding the health care order to the first health care practitioner via the electronic health records application, and instructions for the patient for complying with the health care order; receiving, from the first health care practitioner via one or more input devices associated with the first electronic device, input corresponding to creation of a first health care order which includes first one or more parameters associated with a health care goal for the patient, second one or more parameters associated with one or more rules for communicating notifications regarding the first health care order to the first health care practitioner via the electronic health records application, and first instructions for the patient for complying with the first health care order; displaying, to the patient via a display device associated with a second electronic device, an interface of a patient portal comprising a goals interface which displays information associated with the first health care order for the patient created by the first health care practitioner; receiving, from the patient via the patient portal, an indication of acceptance of the first health care order; receiving, via the patient portal, data for one or more vital readings associated with the first health care order; automatically determining, based on the one or more vital readings, that one of the one or more rules for communicating notifications regarding the first health care order was violated; and automatically communicating, based on the determination that one of the one or more rules was violated, a notification to the electronic health records application; displaying, to the first health care practitioner via a display device associated with the first electronic device, the notification in an interface of the electronic health records application.

In a feature of this aspect, the first electronic device comprises a computer.

In a feature of this aspect, the first electronic device comprises a tablet.

In a feature of this aspect, the first electronic device comprises a phone.

In a feature of this aspect, the first electronic device comprises a touchscreen.

Another aspect relates to a method which includes displaying, to a first health care practitioner via a display device associated with a first electronic device, an interface of an electronic health records application; receiving, from the first health care practitioner via one or more input devices associated with the first electronic device, input corresponding to engagement with an order creation interface element of the displayed interface of the electronic health records application; displaying, to the first health care practitioner via a display device associated with the first electronic device, an order creation interface for creating a health care order configured to allow the first health care practitioner to specify one or more parameters associated with a health care goal for the patient, one or more parameters associated with one or more rules for communicating notifications regarding the health care order to the first health care practitioner via the electronic health records application, and instructions for the patient for complying with the health care order; receiving, from the first health care practitioner via one or more input devices associated with the first electronic device, input corresponding to creation of a first health care order which includes first one or more parameters associated with a health care goal for the patient, second one or more parameters associated with one or more rules for communicating notifications regarding the first health care order to the first health care practitioner via the electronic health records application, and first instructions for the patient for complying with the first health care order; displaying, to the patient via a display device associated with a second electronic device, an interface of a patient portal comprising a goals interface which displays information associated with the first health care order for the patient created by the first health care practitioner; receiving, from the patient via the patient portal, an indication of acceptance of the first health care order; automatically determining, after a period of time has passed in which the patient has not entered any vital readings, that the patient is not complying with the order; and automatically communicating, based on the determination that the patient is not complying with the order, a notification to the electronic health records application; displaying, to the first health care practitioner via a display device associated with the first electronic device, the notification in an interface of the electronic health records application.

Another aspect relates to a method which includes displaying, to a first health care practitioner via a display device associated with a first electronic device, an interface of an electronic health records application; receiving, from the first health care practitioner via one or more input devices associated with the first electronic device, input corresponding to engagement with an order creation interface element of the displayed interface of the electronic health records application; displaying, to the first health care practitioner via a display device associated with the first electronic device, an order creation interface for creating a health care order configured to allow the first health care practitioner to specify one or more parameters associated with a health care goal for the patient, one or more parameters associated with one or more rules for communicating notifications regarding the health care order to the first health care practitioner via the electronic health records application, and instructions for the patient for complying with the health care order; receiving, from the first health care practitioner via one or more input devices associated with the first electronic device, input corresponding to creation of a first health care order which includes first one or more parameters associated with a health care goal for the patient, second one or more parameters associated with one or more rules for communicating notifications regarding the first health care order to the first health care practitioner via the electronic health records application, and first instructions for the patient for complying with the first health care order; automatically determining, after a period of time has passed in which the patient has not accepted the first health care order, that the patient is not complying with the order; and automatically communicating, based on the determination that the patient is not complying with the order, a notification to the electronic health records application; displaying, to the first health care practitioner via a display device associated with the first electronic device, the notification in an interface of the electronic health records application.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

FIGS. 2-8C illustrate an exemplary interface for entering a weight management order;

FIG. 9 illustrates another exemplary interface for entering a weight management order;

FIGS. 11A-15 illustrate exemplary interfaces for entering a weight management order;

FIG. 16 illustrates an exemplary interface for entering a monitor blood pressure order;

FIG. 17 illustrates an exemplary interface for entering a monitor blood glucose order.

FIG. 18 illustrates an exemplary inbox of a patient portal;

FIGS. 19-20 illustrate exemplary goals interfaces for a patient portal;

FIG. 21 illustrates an exemplary consent form indicating that a user accepted a monitor weight goal and declined a maintain blood pressure goal;

FIG. 22 illustrates an exemplary decline goal interface;

FIG. 23 illustrates an exemplary interface for adding a vital reading in connection with one or more goals;

FIGS. 24-25 illustrate display of readings in a goals interface;

FIG. 27 illustrates an exemplary interface for deleting a vital reading;

FIG. 28 illustrates an exemplary interface which includes a warning interface element;

FIGS. 30-31 illustrate exemplary interfaces for adding a blood glucose vital reading;

FIGS. 32-33 illustrate display of blood glucose readings in a goals interface;

FIG. 34 illustrates an exemplary goal interface for a monitor blood pressure order;

FIG. 35 illustrates an exemplary interface for adding a blood pressure vital reading;

FIGS. 36-37 illustrate display of blood pressure readings in a goals interface;

DETAILED DESCRIPTION

Figure 1:
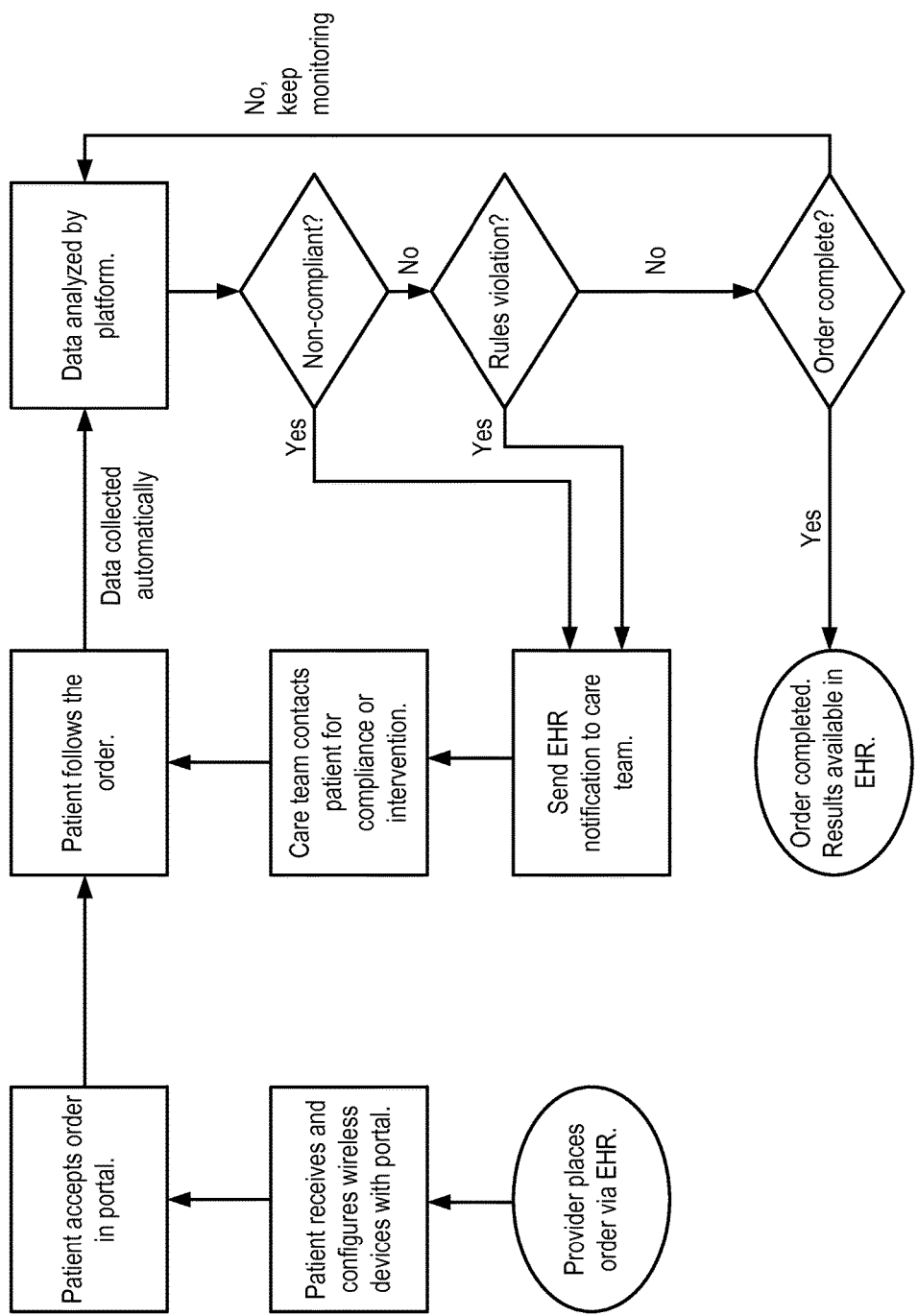
FIG. 1 illustrates a flow for an exemplary methodology in accordance with one or more preferred implementations.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

When a patient is receiving medical treatment, he or she may sometimes be presented with a care plan which will facilitate his treatment. The care plan may include instructions for one or more actions to perform or measurements to take outside of a health care professional's supervision. For example, a patient may be provided a care plan which includes instructions to weigh himself or herself every day, and record the results for eventual review by a health care professional.

Additionally, sometimes, a patient may be presented with a health care goal to meet. For example, a patient may be instructed to try to meet the goal of losing ten pounds over three months. This goal may include related instructions for the patient to weigh himself or herself every morning.

One or more preferred implementations relate to a monitoring and compliance application which improves patient engagement and collaboration between a patient and his or her health care provider. In one or more preferred implementations, such an application is an EHR agnostic solution that leverages existing order entry and results functionality of an EHR.

In an exemplary methodology, orders are created in an EHR for patients to perform home monitoring. The patient is notified of the order and the request will appear as a goal for the patient within a platform portal (such as, for example a web portal or a mobile application). The patient may comply with the order (which might be, for example, to monitor his or her weight daily) utilizing wireless devices (such as a Withings scale) that can communicate data to other devices or to the platform, or by manually entering values into the platform. This home monitoring data is then evaluated against patient specific rules that were configured when the order was placed. Non-compliance of the order or violation of any of the order parameters will result in a notification that is sent back to the ordering provider as a message in the EHR. The notification provides summary information about the order and results allowing the provider to determine if an intervention is necessary. Upon completion of the order, a summary of the results is sent back to the EHR for review by the provider.

A platform in accordance with one or more preferred implementations obviates the need for as many manual processes to monitor patients. By managing patients within a platform and gaining their consent for that monitoring, nurses/coordinators can effectively manage their high-risk populations by exception. In one or more preferred implementations, it is not necessary to create follow up touch points for every patient, as nurses/coordinators will know within half an hour if a patient has failed a rule or is non-compliant. This allows them to focus attention on those patients that require it.

In one or more preferred implementations, a platform provides monitoring tools to notify a provider or care team if a patient is not following an order. Conventionally, it is common for a patient to follow an order but not realize the medical significance of his or her vitals, results, or symptoms. In one or more preferred implementations, a system analyzes this data and will provide a notification (e.g. to a care team) if something is potentially amiss.

In one or more preferred implementations, consumer grade devices are integrated with a platform, or utilized in conjunction with a platform, to monitor a patient at home for variances from expected values. In one or more preferred implementations, integration with one or more EHRs enables communication of notifications back to clinicians in their own workflows so as to allow them to receive such notifications without having to log in to another application.

In one or more preferred implementations, monitoring data is stored at the platform, e.g. as a personal health record. In one or more preferred implementations, a platform is configured to allow data from multiple EHRs to be aggregated at the platform in one patient-specific repository, together with patient input data.

In one or more preferred implementations, an application portal, such as a web portal or a mobile application, is configured for use by patients to manage their care plans. The portal is preferably configured to communicate data related to such care plan back to a health care professional, for example by communicating data back to an electronic health records (EHR) application utilized by the health care professional.

For example, in an exemplary use case, a patient is provided a health care plan which includes the goal of losing ten pounds over three months, and an instruction to measure herself every morning. The patient can access a portal, for example via a web browser or via a mobile application on their phone or tablet, which allows the user to view information associated with the care plan. The portal details the care plan goal and instructions, and facilitates patient compliance with the care plan. The patient can either use a scale to find their weight each morning and manually input it via the portal, or alternatively can utilize a scale that is configured to automatically communicate their weight.

Such automatic communication might, for example, involve communication over a wired line (e.g. via USB), or might involve wireless communication (e.g. via WiFi, Bluetooth, or a cellular network). Such automatic communication might involve communication to a nearby electronic device (such as a computer, laptop, tablet, or phone), or communication to a remote device (such as a remote server).

Weight data from the scale may be automatically communicated to an electronic device for later communication to the portal, or to a device or server associated with the portal. In any event, the weight data is eventually loaded into the portal. Optionally, the portal may automatically review the weight data, and generate one or more notifications or alerts if one or more values lie outside of a threshold. The portal may communicate a notification, either of the presence of data or of an alert, to a health care provider via the EHR application.

FIG. 1 illustrates a flow for an exemplary methodology in accordance with one or more preferred implementations. As illustrated in FIG. 1, first a provider places an order via an EHR. A patient receives the order via a portal and configures wireless devices for use in complying with the order. For example, a user might configure a wireless scale to automatically communicate weight data to an electronic device which in turn communicates it to the portal. The patient accepts the order in the portal, and proceeds to follow the order (for example, proceeds to weight herself every morning). Data is collected automatically as the patient follows the order (for example, by the scale configured to wirelessly communicate data).

In one or more preferred implementations, monitoring rules for an order are established, and measurement data may be automatically evaluated against the monitoring rules to determine if the patient is complying with the order. For example, if the order included a requirement to obtain a blood pressure measurement every morning, and the patient did not do so on a particular day, this might be flagged as non-compliance. Such rules may be established by a health care provider at the time of entering an order, or may be preconfigured in association with a particular type of order. Preconfigured rules may be at least partially user-configurable (e.g. a user may be able to set a value of a variable, etc.).

Further, in one or more preferred implementations, acceptable ranges may be set and a system may be configured to determine whether measurements are outside of such acceptable ranges such that medical intervention may be necessary.

In the event of non-compliance with an order or a determination that a measurement falls outside of an acceptable range, a notification is sent via the EHR. Upon receipt of such a notification, a health care professional can contact the patient to follow up on the non-compliance or rules violation. Once an order is complete, results of the order are available via the EHR. In one or more preferred implementations, ongoing measurements and data are available via the EHR and the portal throughout the course of the order, and the results are additionally available via the portal and EHR upon completion of the order.

For example, consider a patient John Doe who has congestive heart failure. His provider, Dr. Smith, has requested that John monitor his weight every day. John is informed that if his weight increases by 3 pounds in one day or by 5 pounds in 1 week, then he needs to contact his doctor's office. This weight gain indicates fluid retention requiring medical intervention (e.g. John needs to have his medications adjusted). Dr. Smith places an order and provides John with a wireless Withings scale that will automatically send his weight to the system so it can be monitored. John is to take his weight first thing in the morning, wearing similar clothing, using the same scale, after urinating but before eating or drinking. John begins using the scale every morning as directed. During the second week of monitoring, his weight increases from 162.3 on Tuesday to 167.4 on Monday of the following week. John miscalculates and does not realize that his weight has increased by 5 pounds in 1 week. However, the system notices this change and notifies his doctor within minutes of John stepping off the scale. John gets a call later that morning from his doctor's office informing him of the problem and requesting that he make an appointment that day to see his provider. Later that afternoon Dr. Smith adjusts John's medications and his weight returns to 162.5 pounds within a couple of days.

An exemplary system will now be described with respect to exemplary functionality contemplated for congestive heart failure, diabetes, obesity, and hypertension. This system will be described with respect to orders for weight management (gaining or losing weight), weight monitoring (providing notification of weight change), blood pressure monitoring, and blood glucose monitoring. It will be appreciated, however, that these orders are merely exemplary, and additional orders for different disorders are available within the system.

In one or more preferred implementations, a weight management order is provided which is configured to help a patient gain or lose weight over a specified time period.

In one or more preferred implementations, the order includes instructions for a patient to only measure his or her weight once a day, preferably first thing in the morning after urinating but before eating or drinking.

In one or more preferred implementations, several standard weight orders (e.g. "lose 10 pounds in a month" and "lose 15 pounds in two months" may be provided and may or may not be user configurable.

In one or more preferred implementations, a weight management order is configurable via specification of how much weight a patient needs to gain or lose, and how long they have to do it. Preferably, the initial weight, target weight, start date, and end date will all be determined when a first measurement is entered by a patient.

FIG. 2 illustrates an exemplary interface for entering a weight management order. The interface allows a user to specify a goal for the order by interacting with several user interface elements. For example, a user can select whether the goal for the patient is to gain or lose weight via interaction with a drop down user interface element, as illustrated in FIG. 3. Further, a user can increase or decrease a target weight change value via increment and decrement user interface elements, as illustrated in FIG. 4. A user can similarly specify whether a target weight change value is expressed in pounds or kilograms. A user can further specify a time period for a target weight change, as illustrated in FIG. 5.

The interface further allows a user to configure rules for the weight management order. The interface of FIG. 2 includes two rules that a user can toggle on or off using radio button user interface elements, as illustrated in FIG. 6. Each of these rules includes a number of user configurable parameters that a user can adjust utilizing user interface elements, as illustrated in FIG. 7.

The interface is configured to allow a user to edit patient instructions that will be presented to the patient with the order. FIGS. 8A-8C illustrate an exemplary process for editing such patient instructions.

In one or more preferred implementations, an interface for entering a weight management order is configured to allow a user to specify where notifications are to be sent, as illustrated in FIG. 9. Preferably, a user can indicate that notifications are to be sent to themselves and other users or user groups, as illustrated.

In one or more preferred implementations, upon creation of an order, for example via the exemplary order interface of FIG. 2, data for the order is stored at a platform or platform database. This data preferably includes data describing the order and parameters associated therewith.

For example, for an exemplary weight management order, this data includes a parameter which specifies how many times per unit (such as a day), the unit being specified in another parameter, that a measurement needs to be taken.

This data preferably further includes a parameter which specifies a type of the order, e.g. that it is a weight gain order or a weight loss order. This data preferably further includes a parameter which specifies how much weight is to be gained or lost. A separate parameter preferably indicates whether this value represents pounds or kilograms.

This data preferably further includes an order duration parameter and an associated units parameter which together specify the duration of the order (e.g. three weeks, four days, etc.). In one or more preferred alternative implementations, a duration parameter may simply be stored in one format (e.g. days) which is understood to be the format for this parameter.

This data preferably further includes an instructions parameter which stores patient instructions for the order.

This data preferably further includes a status parameter which represents a status of the order. In one or more preferred implementations, a numeric status value is utilized to represent a status. In an exemplary status representation methodology, a status value of 1 indicates that a patient has accepted an order, a status value of 2 indicates that a patient has declined an order, a status value of 0 indicates that a patient has neither accepted nor declined an order, a status value of 4 indicates that an order is complete, and a status value of 3 indicates a status of non-compliance, which might, for example, be the case if a patient has missed certain number of reasons and a notification has been sent to a care team associated with the order. Preferably, the next time a reading is received that counts for the order, the status is changed to 1, indicating that the order has been accepted. This allows for the prevention of repeated notifications for an ongoing non-compliant order, while allowing a second notification to be sent out if a patient fails to comply, finally complies, and then fails to comply again.

This data preferably further includes one or more patient identifiers. These identifiers may comprise, for example, an EHR patient identifier, a platform patient identifier, or a government patient identifier, such as a social security number.

This data preferably further includes one or more provider identifiers. These identifiers may, for example, keep track of the provider that placed the order. This identifier may take the form of a platform provider identifier.

This data preferably further includes an organization identifier, which may identify an organization where an order came from, which might, for example, be useful for determining where to send notifications and results.

This data preferably includes an order number, which is utilized to keep track of the order. In one or more preferred implementations in which an order can be placed from an EHR, an external order identifier parameter is utilized to store an order identifier for an EHR system (e.g. an EHR system internal order identifier).

This data preferably further includes a start date and time parameter which keeps track of the date time that the order was accepted. In one or more preferred implementations, this is stored in UTC time.

This data preferably further includes an initial weight parameter. This parameter is set to the first patient entered weight (e.g. manually input or automatically input from a Withings scale) that is on or after the start date and on or before the end date. In one or more preferred implementations, the initial weight can change, such as, for example, if a patient accepts an order on February 21, enters a weight of 199 pounds on February 22 for February 22, and then later goes back and enters weight on February 23 for both February 21 and February 23 (201 pounds, and 198 pounds, respectively). In this case, the initial weight parameter would be set on February 22 to 199 pounds, but would then be changed to 201 pounds on February 23 when the patient input the weight measurement for February 21.

In one or more preferred implementations, this data further includes a target weight parameter. This target weight represents the initial weight plus or minus the amount of weight to be gained or lost. Preferably, as the initial weight can change, this value is recalculated based on the initial weight and the weight to be gained or lost every time the order is processed or evaluated.

This data preferably further includes an end date parameter. This parameter is preferably calculated by taking the initial date and adding the specified duration of the order (based on the order duration parameter and the associated units parameter) to the initial date. For example, if the initial date was Feb. 28, 2012, and the order duration was two years, the end date would be found by adding two years to the initial date, resulting in an end date of Feb. 28, 2014. Preferably, a calculated end date is validated to ensure that it is a valid date, and if it is not, the next valid date is utilized. For example, if the initial date was Feb. 29, 2012, and the order duration was two years, the end date would be Mar. 1, 2014.

This data preferably further includes a parameter representing a date and time an order was created. This data preferably further includes a parameter representing a date and time an order was last updated.

This data preferably further includes a parameter specifying whether a notification is to be sent for missed readings. This data preferably further includes a parameter specifying a number of readings that need to be missed before a notification is sent. In one or more preferred implementations, this data further includes a parameter specifying the date and time of the last notification for one or more missed readings. In one or more preferred implementations, this is utilized to determine whether another notification needs to be sent. For example, if a notification was sent because a patient missed a reading seven days in a row, and then seven more days pass and the patient has missed seven more readings, this parameter can be utilized to determine that another notification should be sent.

This data preferably further includes a parameter specifying whether a notification should be sent if an order hasn't been accepted. This data preferably further includes a number of days after the order creation date that need to have passed before a notification is sent that a patient has not accepted an order. In one or more preferred implementations, this data further includes a parameter specifying the date and time of the last notification for non-acceptance. In one or more preferred implementations, this is utilized to determine whether another notification needs to be sent. For example, if a notification was sent because a patient had not accepted an order after seven days, and then seven more days pass and the patient still has not accepted the order, this parameter can be utilized to determine that another notification should be sent.

Preferably, an order is periodically evaluated even if no new measurements or information is obtained. For example, an order is preferably periodically evaluated to determine whether a user has failed to comply with an order and a notification of this should be sent. Preferably, the data further includes a parameter specifying the last date and time an order was evaluated or analyzed, which can be utilized, for example, to trigger an evaluation for non-compliance.

The data preferably further includes a parameter specifying the last analysis scheduled.

Preferably, data is stored for weight readings (e.g. manually input weight measurements or automatically input weight measurements from a Withings scale) together with a date and time the reading was taken, although in one or more preferred implementations a time value is optional. Preferably, for measurements received from a Withings scale, a date and time will be downloaded together with a weight measurement, as data from a Withings scale may sometimes be communicated one or more days after a measurement. Preferably, for manually input weight measurements, a date and time the measurement was taken will be input as well, but in at least some implementations a date and time the reading was input may be utilized if no date and/or time was input.

Preferably, weight readings on or after the initial date and on or before the end date are considered for the order, but weight readings without an associated date are not considered. In one or more preferred implementations, a single weight reading for a patient may be associated with or stored in association with multiple orders for that patient.

An exemplary methodology for order analysis will now be described. Preferably, orders are analyzed using a patient's time zone in order to ensure that the definition of a day, week, or month is consistent based on where the patient is located and not influenced by where a provider is located.

Preferably, an order is periodically evaluated or analyzed to determine a status of the order, e.g. whether it has not been accepted, is not being complied with, or has been completed.

An order is determined to be in a not accepted state if the order has been created and no acceptance has been received. In this state, a notification will be sent out if a specified number of days have passed since the order creation without the order having been accepted, or if that specified number of days have passed since the last notification of non-acceptance was sent out. If a notification of non-acceptance is sent out, a parameter indicating the last time a notification of non-acceptance was sent out is preferably updated.

An order is determined to be in a non-compliant state if, for example, the current date (in the patient's time zone) minus the reading date associated with the most recent reading (in the patient's time zone) is greater than or equal to the number of consecutive readings that need to be missed in order to trigger non-compliance. If an order is determined to be non-compliant, a notification is preferably sent, and the date and time of the notification is stored. Subsequently, if the current date minus the date of the last notification is greater than or equal to the number of consecutive readings that need to be missed in order to trigger non-compliance, then another notification is sent, and the date and time of the notification is stored.

For orders in a non-compliant state, if a new reading is received which was added after the last evaluation date, then the status of the order is set to accepted and the order is evaluated.

For any order with a status of accepted or not compliant, if the current date is after the order end date, then the order is marked completed.

In one or more preferred implementations, an order is also preferably evaluated when data associated with a new reading is received.

Figure 10:
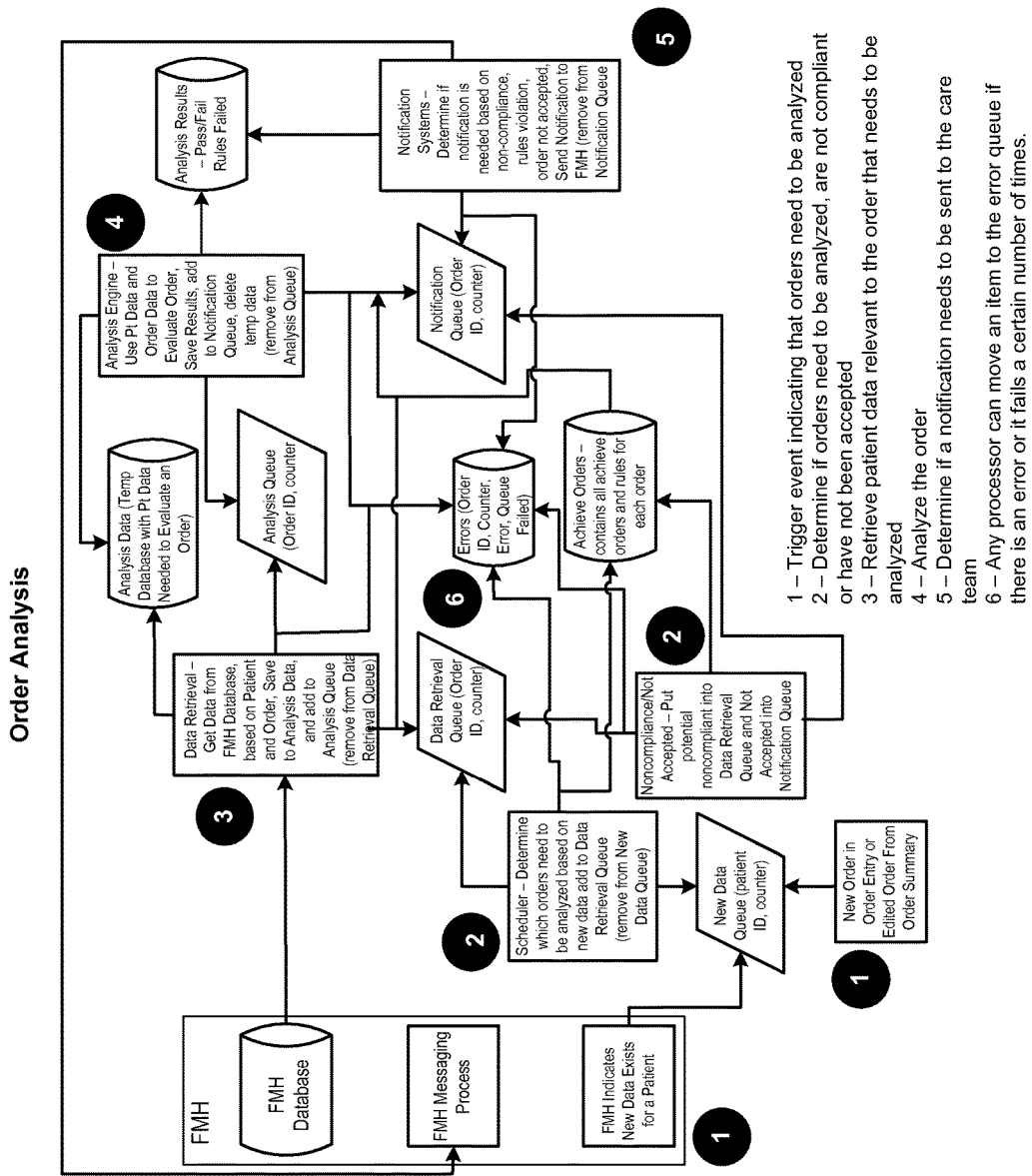
FIG. 10 illustrates an exemplary flow for order analysis.

FIG. 10 illustrates an exemplary flow for order analysis.

In one or more preferred implementations, a monitor weight order is provided which is configured to facilitate monitoring of a patient's weight over a specified time period and provide notifications based on changes. FIG. 11A illustrates an exemplary interface for entering a weight management order.

The interface of FIG. 11A allows a user to specify how long weight is to be taken for (a duration of the order), as well as various rules for notifications for the order. For example, the interface of FIG. 11A allows a user to specify that a notification should be sent if a patient's weight "increases", "decreases", or "increases or decreases" a specified amount over a specified time period, as illustrated in FIG. 11B.

In one or more preferred implementations, an interface is configured to allow a user to add rules to an order, as illustrated in FIG. 12. The interface may be configured to allow a user to add a specific type of rule, such as, for example, a weight change notification rule, a missed reading notification rule, or a failure to consent notification rule, as illustrated in FIG. 13. In one or more preferred implementations, a user is even able to add a custom rule with fields and parameters of their choosing. FIG. 14 illustrates addition of a weight change notification rule to the interface of FIG. 12.

In one or more preferred implementations, an interface may additionally be configured to allow a user to remove rules, as illustrated in FIG. 15.

It will be appreciated that notifications might be sent for multiple rules associated with a single order. In one or more preferred implementations, data for the order includes data keeping track of notifications sent for each rule of the order. In one or more preferred implementations, sending out a notification for a first rule of an order does not preclude sending out a second notification for a second rule of the same order, while in one or more preferred implementations, it may. In one or more preferred implementations, this may be user configurable. Preferably, data for an order includes data for each notification that is sent, including information relating to which rule triggered communication of the notification.

In one or more preferred implementations, if during an order evaluation it is determined that multiple rules are triggered, information relating to all of the rules that have been triggered is included in a single notification, rather than having multiple notifications be sent, although in at least some implementations, multiple notifications may be sent.

An exemplary methodology for evaluating a rule includes first finding all readings that were taken after the order start date up until the order end date, which can be characterized as an order reading set. The readings are then cycled through in reverse chronological order, with the newest readings evaluated first. For each respective reading, a date and time for the reading is determined, and the rule period is subtracted from this date and time. For example, if the rule involves monitoring to determine if weight increases by three pounds in three days, then the rule period would be three days. Subtracting the rule period from the date and time associated with the respective reading sets a date starting point for consideration of that rule for that respective reading, although this date starting point cannot be before the order starting date. Next, all readings that occurred on or after the date starting point but before the date and time associated with the respective reading are loaded as a reading set, and each reading in the reading set is evaluated against the respective reading. If the rule is configured to determine if weight increases a set rule amount, then the process involves evaluating whether the respective reading value minus any value in the reading set is greater than or equal to the set rule amount (or whether any value in the reading set plus the set rule amount is greater than or equal to the respective reading value). If the rule is configured to determine if weight decreases a set rule amount, then the process involves evaluating whether any value in the reading set minus the respective reading value is greater than or equal to the set rule amount (or whether any value in the reading set minus the set rule amount is less than or equal to the respective reading value). In one or more preferred implementations, if the rule is configured to determine if weight increases or decreases a set rule amount, this is evaluated as if evaluating both an increases rule and a decreases rule, while in one or more alternative preferred implementations, the process involves evaluating whether the absolute value of any value in the reading set minus the respective reading value (or vice versa) is greater than or equal to the set rule amount.

This process is repeated for each reading in the order reading set, although it may be cut short if a determination is made that the rule has been violated. This process is then repeated for other rules of the order.

In one or more preferred implementations, a monitor blood pressure order is provided which is configured to facilitate monitoring of a patient's blood pressure over a specified time period and provide notifications based on changes. FIG. 16 illustrates an exemplary interface for entering a monitor blood pressure order. As illustrated, the interface allows a user to specify a goal for a patient, e.g. to have a blood pressure higher than specified values, or lower than specified values.

In one or more preferred implementations, a monitor blood glucose order is provided which is configured to facilitate monitoring of a patient's blood glucose over a specified time period and provide notifications based on changes. FIG. 17 illustrates an exemplary interface for entering a monitor blood glucose order.

As illustrated, the interface allows a user to specify times when a patient should take a blood glucose reading. The interface further allows a user to specify target ranges for each of these times. For example, an order may instruct a user to take a blood glucose reading one to two hours after meals, and indicate that the target range for a blood glucose reading taken at such a time is 60 to 179 mg/dL. In one or more preferred implementations, an interface allows a user to add additional target ranges (e.g. for other measurement times).

The interface further allows a user to specify rules for the order which may trigger notifications. For example, the interface allows a user to specify that if a patient fails to make a specified percentage of readings over a specified time period, then a notification should be sent out.

The interface further allows a user to specify conditions for when a notification should be sent out in response to a reading outside of a defined range. For example, the interface allows a user to specify that a notification should be sent out if a reading is a specified amount outside of a target range, or if any reading is outside of a specified range.

Figure 18:
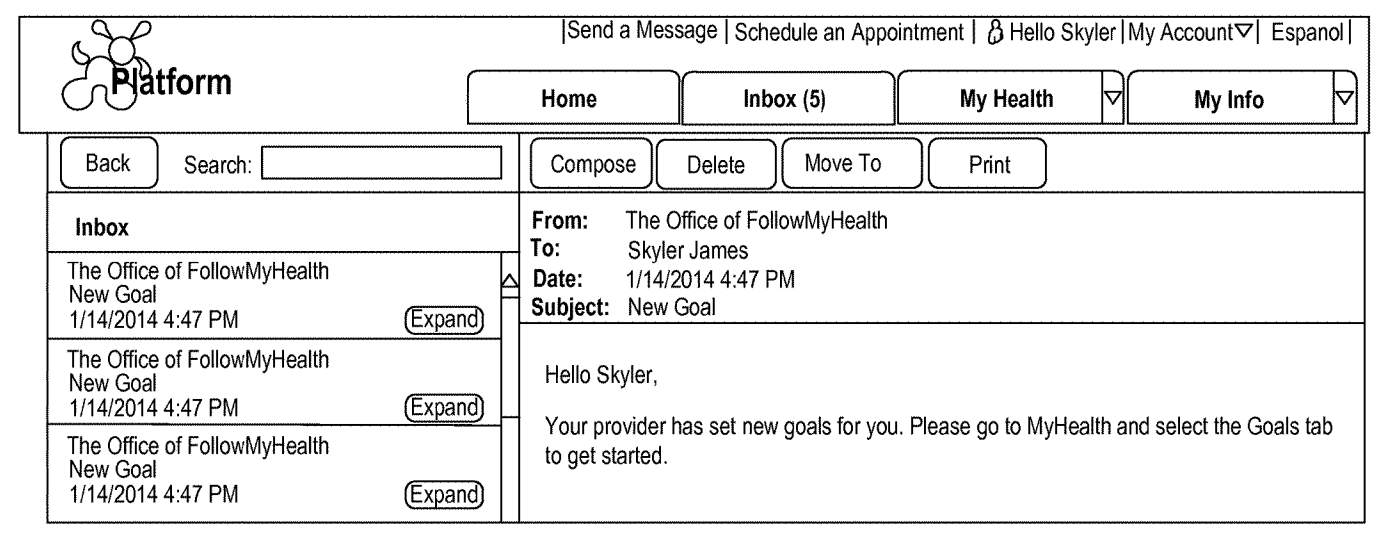

In one or more preferred implementations, a system preferably includes a patient portal that allows a patient to log in and view orders that have been created for them. Preferably, when a new order is created for a patient, an electronic message informing them of the new order is generated and communicated to the patient, for example to an inbox of the patient portal or to an email address associated with the patient. FIG. 18 illustrates an exemplary inbox of a patient portal which includes such a communication.

In one or more preferred implementations, a patient portal preferably includes a goals interface which relates to orders placed by a provider (e.g. via an EHR). These orders are presented to patients via the patient portal as goals. For example, they might have a goal to keep their blood pressure below a certain level, or lose a certain amount of weight.

Figure 19:
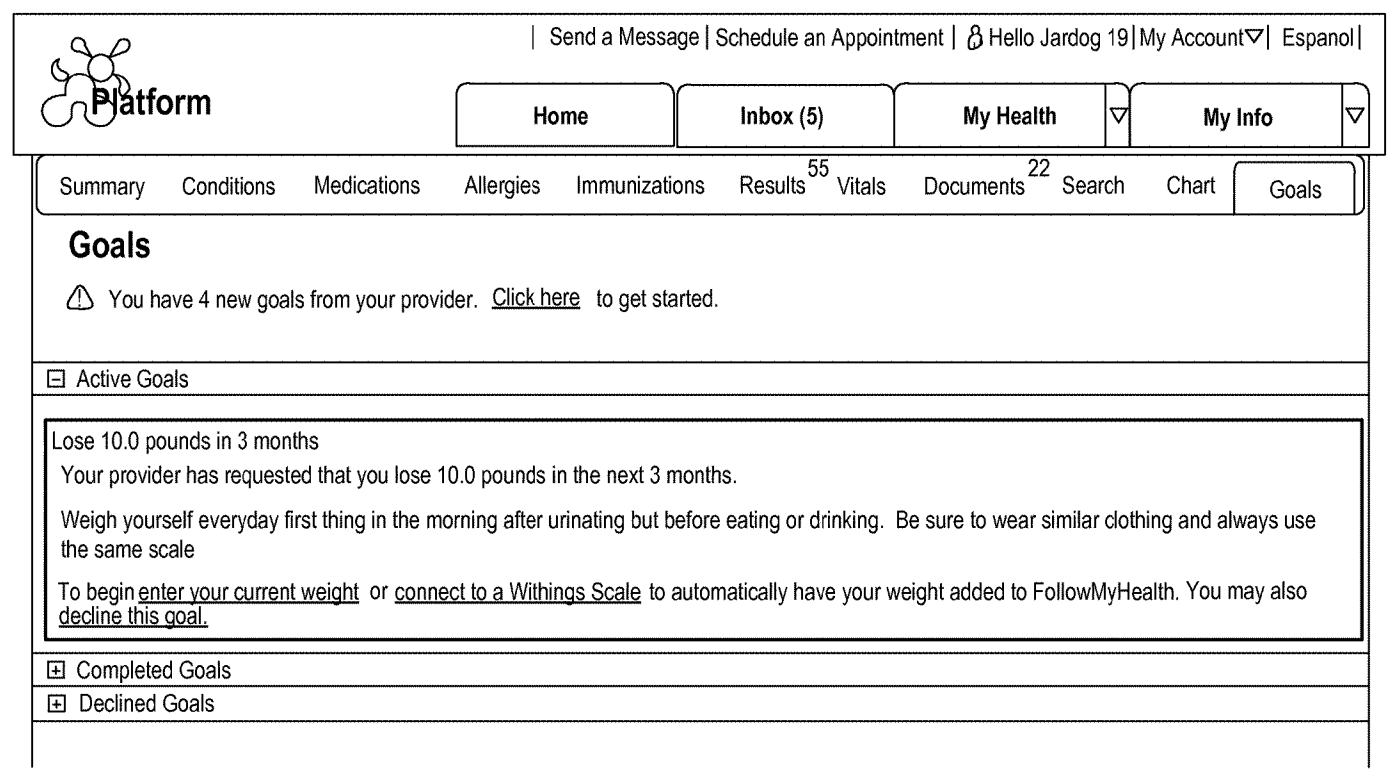

FIG. 19 illustrates an exemplary goals interface for a patient portal. The goals interface preferably includes elements configured to allow a user to view completed and declined goals, as illustrated. The goals interface preferably further includes elements configured to allow a user to view active goals, should they have any active goals.

The goals interface informs a user if they have any new goals, and prompts them to get started on those goals if they do. Upon clicking on such prompt, a user is presented with a new goals interface which allows the user to accept or decline new goals, as illustrated in FIG. 20. The new goals interface presents the new goals that have not yet been accepted or declined, and allows a user to accept or decline each goal.

Preferably, once a user has accepted or declined each goal, a consent form is automatically generated for each provider which indicates the acceptance or declining of each goal for that provider. If the new goals interface included goals for multiple providers, then a separate consent form will be generated for each provider. FIG. 21 illustrates an exemplary consent form indicating that a user accepted a monitor weight goal and declined a maintain blood pressure goal.

Returning to FIG. 19, the goals interface illustrates an active goal for the user of losing fifteen pounds in four months. Notably, a user can decline this goal via this interface, even though it is already active. Clicking on a link to decline this goal will bring up a decline goal interface, as illustrated in FIG. 22. Declining this goal will generate another consent form indicating that this goal was declined.

Returning once more to FIG. 19, this goal has been accepted but has not yet been started because a reading has not yet been entered. To proceed, a user would need to either enter his or her weight, or connect a Withings scale.

Figure 24:
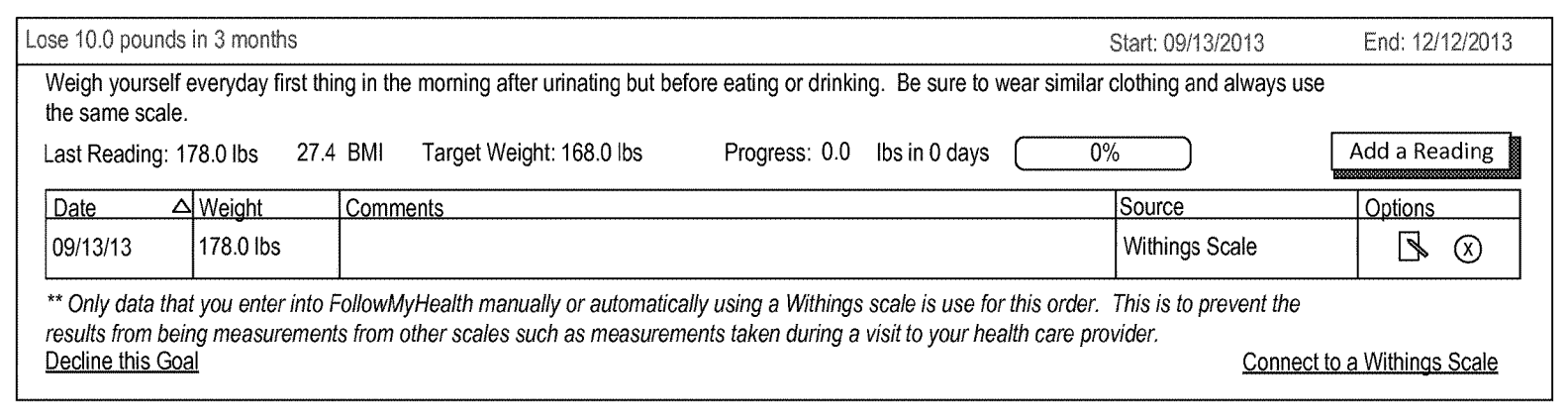

FIG. 23 illustrates an exemplary interface for adding a vital reading in connection with one or more goals. The add vital interface allows the user to specify what type of vital he is providing input for (e.g. weight, blood pressure, etc.), and further allows a user to specify a reading value, a date the reading was taken, and comments for the reading. Once the first reading is input that counts for a goal, that goal has been started, and the readings for that goal are displayed on the goal interface, as illustrated in FIG. 24. Over time, hopefully, a plurality of readings will be entered into the system, either manually or via a Withings scale, as illustrated in FIG. 25.

Figure 26:
FIG. 26 illustrates an exemplary interface for editing a vital reading.

This interface preferably includes user interface elements configured to allow a user to edit a reading. Interacting one of these user interface elements brings up an edit vital interface, as illustrated in FIG. 26. In one or more preferred implementations, however, a user is only able to edit previously entered vital measurements if they were not automatically loaded from another source, such as a Withings scale. In one or more preferred implementations, data automatically loaded from a Withings scale or other similar system must be edited through a system or portal associated with the device, in order to avoid sync issues.

The interface preferably further includes user interface elements configured to allow a user to delete readings. Preferably, however, this will only delete the readings in the user's portal, and will not delete readings from a provider's EHR. FIG. 27 illustrates an exemplary interface for confirming a delete operation.

While FIG. 25 illustrates an exemplary interface for a weight loss order, FIG. 28 illustrates an exemplary interface for a monitor weight order. Preferably, the same weight readings are potentially applicable to both orders, and separate weight readings will not necessarily need to be input for each order, even though the orders may have separate start and end dates. As illustrated in FIG. 28, for the monitor weight order, a statement related to the rules set for the monitoring is included on the interface for the user to see. Further, any reading which triggers a rule violation is preferably indicated via a warning interface element, as illustrated in FIG. 28. A user can preferably hover over such a warning interface element to view details related to the warning, as illustrated.

Figure 29:
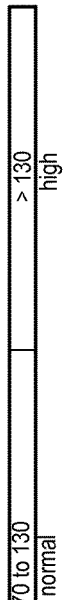
FIG. 29 illustrates an exemplary goal interface for a monitor blood glucose order.
Figure 30:

FIG. 29 illustrates another goal interface for a monitor blood glucose order. The goal interface for the monitor blood glucose order includes one or more graphical elements indicating ranges that the patient should aim to keep his or her blood glucose levels within. A user can input blood glucose readings manually or by using a blood glucose meter which can be specially configured similarly to a Withings scale, such as a Telcare blood glucose meter. When inputting a blood glucose reading, a user can tag the blood glucose reading to indicate when the reading was taken, as illustrated in FIG. 30. In one or more preferred implementations, a drop down user interface element is configured to allow a user to tag when the reading was taken, as illustrated in FIG. 31. Preferably, the drop down user interface element includes an option to leave the field blank.

Once the first reading is input that counts for a goal, that goal has been started, and the readings for that goal are displayed on the goal interface, as illustrated in FIG. 32. Over time, hopefully, a plurality of readings will be entered into the system, either manually or via a specially configured blood glucose monitor, as illustrated in FIG. 33.

FIG. 34 illustrates another goal interface for a maintain blood pressure order. For this order, a user can input blood pressure readings manually or by using a specially configured blood pressure device such a Withings blood pressure monitor. FIG. 35 illustrates an exemplary interface for adding a blood pressure vital reading.

Once the first reading is input that counts for a goal, that goal has been started, and the readings for that goal are displayed on the goal interface, as illustrated in FIG. 36. Over time, hopefully, a plurality of readings will be entered into the system, either manually or via a specially configured blood pressure monitor, as illustrated in FIG. 37. Additionally, in one or more preferred implementations, readings may be entered by a health care provider, as illustrated in FIG. 37, in which a reading taken on Oct. 15, 2013 was entered by a Jardogs Clinic health care provider.

In one or more preferred implementations, a platform is configured to communicate notifications when an order is not being followed or a rule for an order has been violated. Preferably, the platform analyzes an order when data (e.g. in the form of a reading) comes in for that order, as well as periodically (e.g. to check for non-compliance with the order). Preferably, if it is determined that a notification is to be sent for a particular patient for a particular order, then a notification message is queued up in a queue. The platform then preferably waits a predetermined period, such as fifteen minutes, to determine if any additional notification messages need to be sent for that patient. After expiration of the period, the platform will preferably bundle together any notifications for the same patient for the same order for the same provider and send the bundled notification to the provider (and/or another entity that it is indicated a notification should be sent to).

In one or more preferred implementations, there are four basic types of notifications. A first is a declined notification, which notifies a provider that an order has been declined. A second is a not accepted notification, which notifies a provider that an order has not been accepted after a specified number of days. A third is a non-compliant notification, which notifies a provider that a patient has accepted a notification but is not complying with the order and has missed the number of readings specified to trigger a notification. A fourth is a broken rule notification, which indicates that a rule associated with the order has been violated. This type of notification indicates to the provider that something may be wrong, and may require follow up.

These notifications may take the form of a notification to a provider within an EHR application, or an electronic communication to a provider, such as an email or text message.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method comprising:
(a) displaying, to a first health care practitioner via a display device associated with a first electronic device, an interface of a first electronic health records application;
(b) receiving, from the first health care practitioner via one or more input devices associated with the first electronic device, input corresponding to engagement with an order creation interface element of the displayed interface of the first electronic health records application;
(c) displaying, to the first health care practitioner via a display device associated with the first electronic device, an order creation interface for creating a health care order configured to allow the first health care practitioner to specify
    (i) one or more parameters associated with a health care goal for the patient,
    (ii) one or more parameters associated with rules for communicating notifications regarding the health care order to the first health care practitioner via the electronic health records application, and
    (iii) instructions for the patient for complying with the health care order;
(d) receiving, from the first health care practitioner via one or more input devices associated with the first electronic device, input corresponding to creation of a first health care order which includes
    (i) first one or more parameters associated with a first health care goal for the patient,
    (ii) second one or more parameters associated with one or more rules for communicating notifications regarding the first health care order to the first health care practitioner via the first electronic health records application, the one or more rules including rules governing
        (A) communication of a notification that the first health care order has not been accepted a first number of days after its creation, the first number of days being specified by a parameter of the second one or more parameters,
        (B) communication of a notification that no reading has been input by the patient for a second number of days, the second number of days being specified by a parameter of the second one or more parameters, and
        (C) communication of a notification if a reading is outside of a target range specified by one or more parameters of the second one or more parameters; and
    (iii) first instructions for the patient for complying with the first health care order;
(e) displaying, to a second health care practitioner via a display device associated with a second electronic device, an interface of a second electronic health records application;
(f) receiving, from the second health care practitioner via one or more input devices associated with the second electronic device, input corresponding to engagement with an order creation interface element of the displayed interface of the second electronic health records application;
(g) displaying, to the second health care practitioner via a display device associated with the second electronic device, an order creation interface for creating a health care order configured to allow the first health care practitioner to specify
  (i) one or more parameters associated with a health care goal for the patient,
  (ii) one or more parameters associated with rules for communicating notifications regarding the health care order to the first health care practitioner via the electronic health records application, and
  (iii) instructions for the patient for complying with the health care order;
(h) receiving, from the second health care practitioner via one or more input devices associated with the second electronic device, input corresponding to creation of a second health care order which includes
  (i) third one or more parameters associated with a first health care goal for the patient,
  (ii) fourth one or more parameters associated with one or more rules for communicating notifications regarding the first health care order to the first health care practitioner via the second electronic health records application, the one or more rules including rules governing
    (A) communication of a notification that the first health care order has not been accepted a first number of days after its creation, the first number of days being specified by a parameter of the second one or more parameters,
    (B) communication of a notification that no reading has been input by the patient for a second number of days, the second number of days being specified by a parameter of the second one or more parameters, and
    (C) communication of a notification if a reading is outside of a target range specified by one or more parameters of the second one or more parameters; and
  (iii) second instructions for the patient for complying with the second health care order;
(i) displaying, to the patient via a display device associated with a third electronic device, an interface of a patient portal comprising a goals interface which displays information associated with the first health care order for the patient created by the first health care practitioner;
(j) receiving, from the patient via the patient portal, an indication of acceptance of the first health care order;
(k) displaying, to the patient via the patient portal, the first health care goal for the patient and the first instructions for the patient for complying with the first health care order;
(l) receiving data for one or more vital readings associated with the first health care order;
(m) automatically determining, as a first determination, that one of the readings is outside of a target range specified by one or more parameters of the second one or more parameters;
(n) automatically communicating, based on the first determination, a notification to the first health care practitioner;
(o) displaying, to the patient via a display device associated with the third electronic device, an interface of the patient portal comprising a goals interface which displays information associated with the second health care order for the patient created by the second health care practitioner;
(p) receiving, from the patient via the patient portal, an indication of acceptance of the second health care order;
(q) receiving data for one or more vital readings associated with the second health care order;
(r) automatically determining, as a second determination, that one of the readings is outside of a target range specified by one or more parameters of the fourth one or more parameters; and
(s) automatically communicating, based on the second determination, a notification to the second health care practitioner.

2. The method of claim 1, wherein the first electronic device comprises a touchscreen.

3. The method of claim 1, wherein the health care goal for the patient comprises losing or gaining weight.

4. The method of claim 1, wherein receiving data for one or more vital readings associated with the first health care order comprises receiving data input by the patient via the patient portal.

5. The method of claim 1, wherein receiving data for one or more vital readings associated with the first health care order comprises receiving data from an electronic measurement device.

6. The method of claim 5, wherein the electronic measurement device comprises a scale.

7. The method of claim 5, wherein the electronic measurement device comprises a blood pressure monitor.

8. The method of claim 5, wherein the electronic measurement device comprises a blood glucose meter.

9. A method comprising:
(a) displaying, to a first health care practitioner via a display device associated with a first electronic device, an interface of a first electronic health records application;
(b) receiving, from the first health care practitioner via one or more input devices associated with the first electronic device, input corresponding to engagement with an order creation interface element of the displayed interface of the first electronic health records application;
(c) displaying, to the first health care practitioner via a display device associated with the first electronic device, an order creation interface for creating a health care order configured to allow the first health care practitioner to specify
  (i) one or more parameters associated with a health care goal for the patient,
  (ii) one or more parameters associated with rules for communicating notifications regarding the health care order to the first health care practitioner via the electronic health records application, and
  (iii) instructions for the patient for complying with the health care order;
(d) receiving, from the first health care practitioner via one or more input devices associated with the first electronic device, input corresponding to creation of a first health care order which includes
  (i) first one or more parameters associated with a first health care goal for the patient,
  (ii) second one or more parameters associated with one or more rules for communicating notifications regarding the first health care order to the first health care practitioner via the first electronic health records application, the one or more rules including rules governing (A) communication of a notification that the first health care order has not been accepted a first number of days after its creation, the first number of days being specified by a parameter of the second one or more parameters, (B) communication of a notification that no reading has been input by the patient for a second number of days, the second number of days being specified by a parameter of the second one or more parameters, and (C) communication of a notification if a reading is outside of a target range specified by one or more parameters of the second one or more parameters; and (iii) first instructions for the patient for complying with the first health care order;

(e) displaying, to a second health care practitioner via a display device associated with a second electronic device, an interface of a second electronic health records application;

(f) receiving, from the second health care practitioner via one or more input devices associated with the second electronic device, input corresponding to engagement with an order creation interface element of the displayed interface of the second electronic health records application;

(g) displaying, to the second health care practitioner via a display device associated with the second electronic device, an order creation interface for creating a health care order configured to allow the first health care practitioner to specify
 (i) one or more parameters associated with a health care goal for the patient,
 (ii) one or more parameters associated with rules for communicating notifications regarding the health care order to the first health care practitioner via the electronic health records application, and
 (iii) instructions for the patient for complying with the health care order;

(h) receiving, from the second health care practitioner via one or more input devices associated with the second electronic device, input corresponding to creation of a second health care order which includes
 (i) third one or more parameters associated with a first health care goal for the patient,
 (ii) fourth one or more parameters associated with one or more rules for communicating notifications regarding the first health care order to the first health care practitioner via the second electronic health records application, the one or more rules including rules governing (A) communication of a notification that the first health care order has not been accepted a first number of days after its creation, the first number of days being specified by a parameter of the second one or more parameters, (B) communication of a notification that no reading has been input by the patient for a second number of days, the second number of days being specified by a parameter of the second one or more parameters, and (C) communication of a notification if a reading is outside of a target range specified by one or more parameters of the second one or more parameters; and (iii) second instructions for the patient for complying with the second health care order;

(i) displaying, to the patient via a display device associated with a third electronic device, an interface of a patient portal comprising a goals interface which displays information associated with the first health care order for the patient created by the first health care practitioner and information associated with the second health care order for the patient created by the second health care practitioner;

(j) receiving, from the patient via the patient portal, an indication of acceptance of the first health care order;

(k) displaying, to the patient via the patient portal, the first health care goal for the patient and the first instructions for the patient for complying with the first health care order;

(l) receiving data for one or more vital readings associated with the first health care order;

(m) automatically determining that one of the readings is outside of a target range specified by one or more parameters of the second one or more parameters; and (n) automatically communicating, based on the determination, a notification to the first health care practitioner.

10. A method, the method being implemented for a system that includes a plurality of electronic health records applications and a patient portal platform, the method including an improvement comprising configuring the patient portal platform to
 (a) receive orders input via any of the plurality of electronic health records applications, and
 (b) communicate order information for a respective received order, including vital readings, back to a respective electronic health records applications from which the respective order was received,
 (c) such that the patient portal platform can be characterized as being electronic health records application agnostic.

* * * * *